(12) United States Patent
Jovanovich et al.

(10) Patent No.: US 6,423,536 B1
(45) Date of Patent: Jul. 23, 2002

(54) LOW VOLUME CHEMICAL AND BIOCHEMICAL REACTION SYSTEM

(75) Inventors: Stevan B. Jovanovich, Livermore; David J. Roach, Los Gatos; Andrew G. Hadd, San Jose; Bo E. R. Hellman, Palo Alto, all of CA (US)

(73) Assignee: Molecular Dynamics, Inc., Sunnyvale, CA (US)

( * ) Notice: Subject to any disclaimer, the term of this patent is extended or adjusted under 35 U.S.C. 154(b) by 0 days.

(21) Appl. No.: 09/577,199

(22) Filed: May 23, 2000

Related U.S. Application Data
(60) Provisional application No. 60/146,732, filed on Aug. 2, 1999.

(51) Int. Cl.[7] ............................. C12M 1/36; C12P 19/34
(52) U.S. Cl. ....................... 435/287.2; 435/6; 435/91.2; 435/286.2; 435/286.4; 435/287.3; 435/288.4; 435/303.1; 435/305.3; 435/809; 422/63; 422/72; 422/100; 422/102; 422/104; 436/47; 204/453; 204/604
(58) Field of Search ........................ 435/6, 91.2, 286.1, 435/4, 286.2, 286.4, 286.5, 287.2, 287.3, 288.1, 288.4, 303.1, 304.1, 305.2, 305.3, 809; 422/63–67, 72, 100, 102, 104; 436/45, 47, 180; 219/392, 399, 400, 428; 204/451, 453, 601, 604

(56) References Cited

U.S. PATENT DOCUMENTS

| | | | |
|---|---|---|---|
| 3,915,652 A | 10/1975 | Natelson | ....................... 23/259 |
| 4,960,566 A | * 10/1990 | Mochida | |
| 5,273,718 A | * 12/1993 | Skold et al. | |
| 5,455,175 A | 10/1995 | Wittwer et al. | .......... 435/286.1 |
| 5,498,392 A | 3/1996 | Wilding et al. | ............. 422/68.1 |
| 5,560,811 A | 10/1996 | Briggs et al. | ................ 204/451 |
| 5,720,923 A | 2/1998 | Haff et al. | .................. 422/68.1 |
| 5,785,926 A | 7/1998 | Seubert et al. | .............. 422/100 |
| 5,830,657 A | 11/1998 | Leushner et al. | ............... 435/6 |
| 5,840,573 A | 11/1998 | Fields | ...................... 435/287.2 |
| 5,846,727 A | 12/1998 | Soper et al. | .................... 435/6 |
| 5,856,100 A | * 1/1999 | Hayashizaki | |
| 5,897,842 A | 4/1999 | Dunn et al. | .................. 422/131 |
| 5,927,547 A | 7/1999 | Papen et al. | ................... 222/57 |
| 5,968,331 A | * 10/1999 | Kambara et al. | |

FOREIGN PATENT DOCUMENTS

| | | |
|---|---|---|
| WO | WO 92/20778 | 11/1992 |
| WO | WO 98/54292 | 12/1998 |

* cited by examiner

*Primary Examiner*—William H. Beisner
(74) *Attorney, Agent, or Firm*—Thomas Schneck; David M. Schneck

(57) ABSTRACT

A method and device for preparing nanoscale reactions. An automated system utilizes an array of reaction chambers. The ends of the chambers are temporarily sealed with deformable membranes and reactions effected by incubation or temperature cycling. Reaction mixtures may be assembled by using the reaction containers to meter reaction components. After the reaction is finished, the reaction containers may be dispensed onto a substrate and the reaction products analyzed. An automated transfer device may be used for automated transport of the reaction container array or other transportable elements.

64 Claims, 20 Drawing Sheets

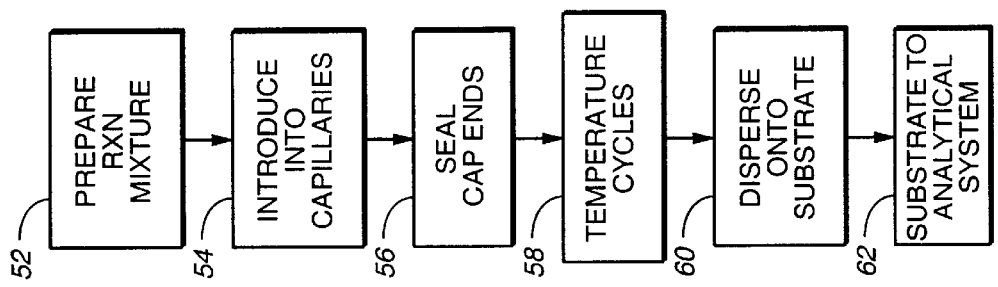
FIG._2
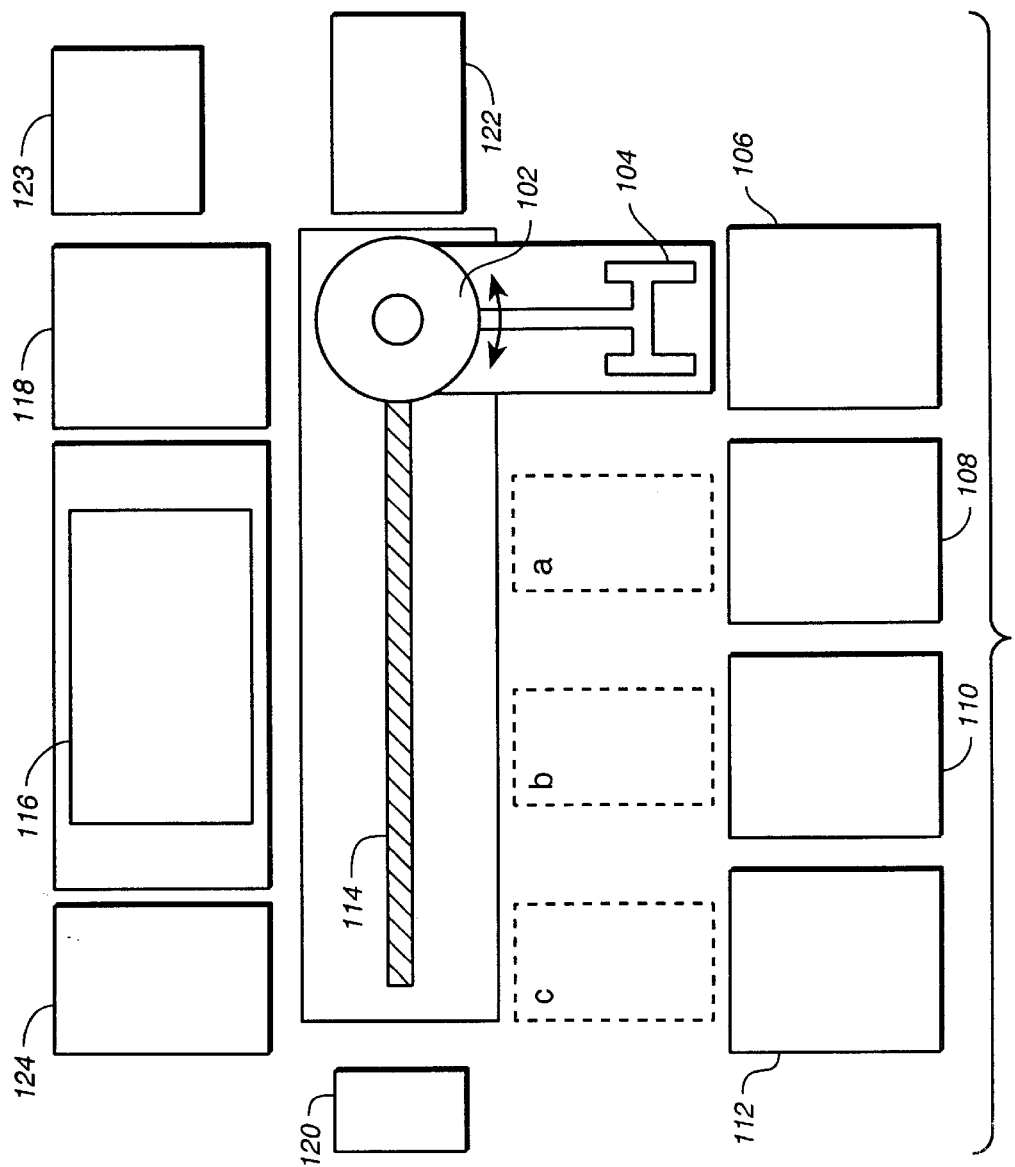
FIG._1

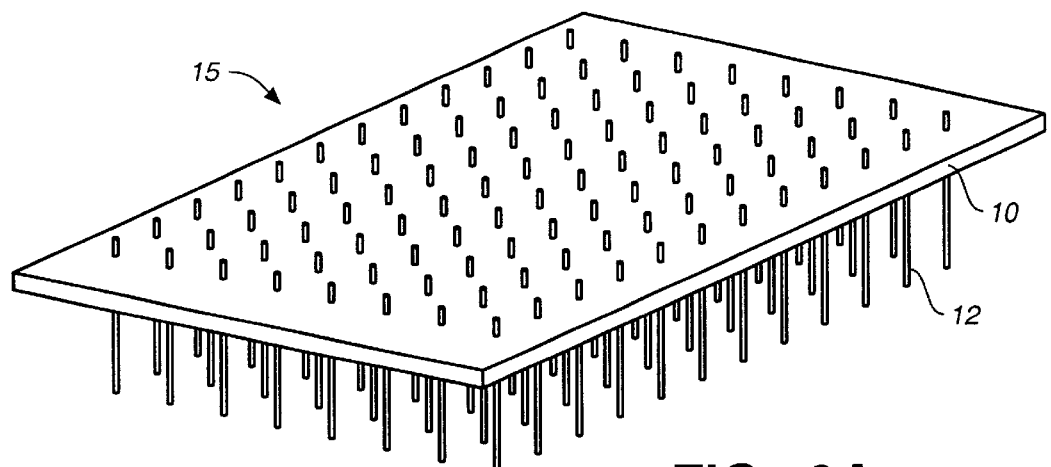
FIG._3A
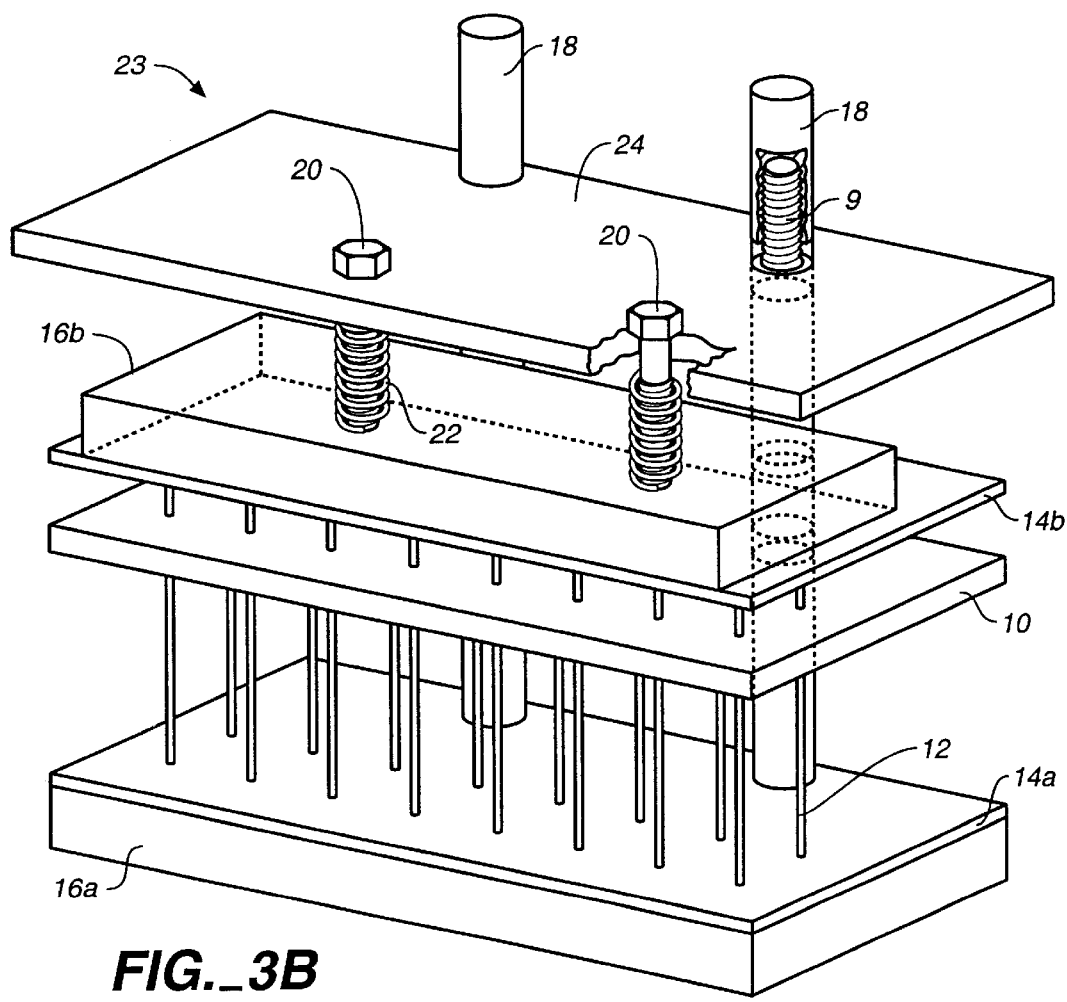
FIG._3B

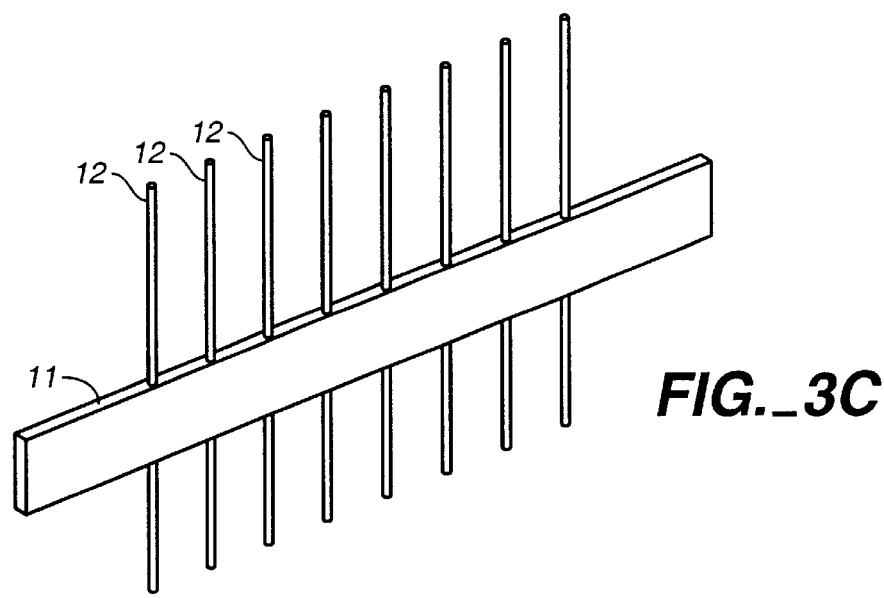
FIG._3C
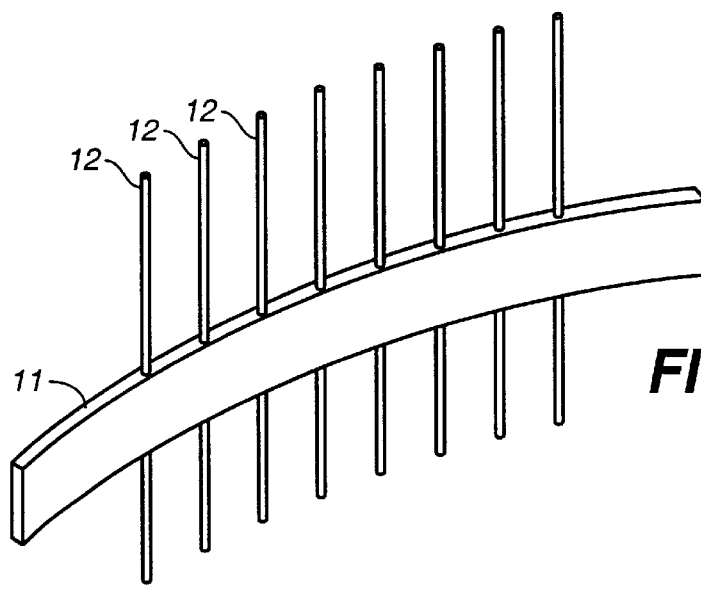
FIG._3D
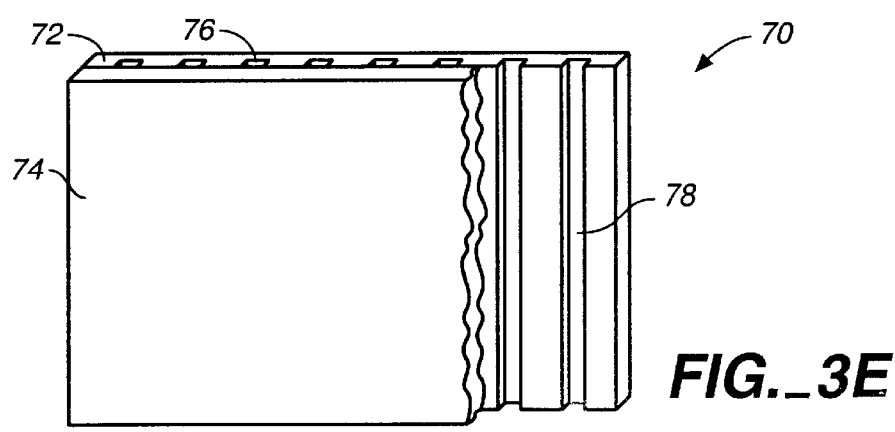
FIG._3E

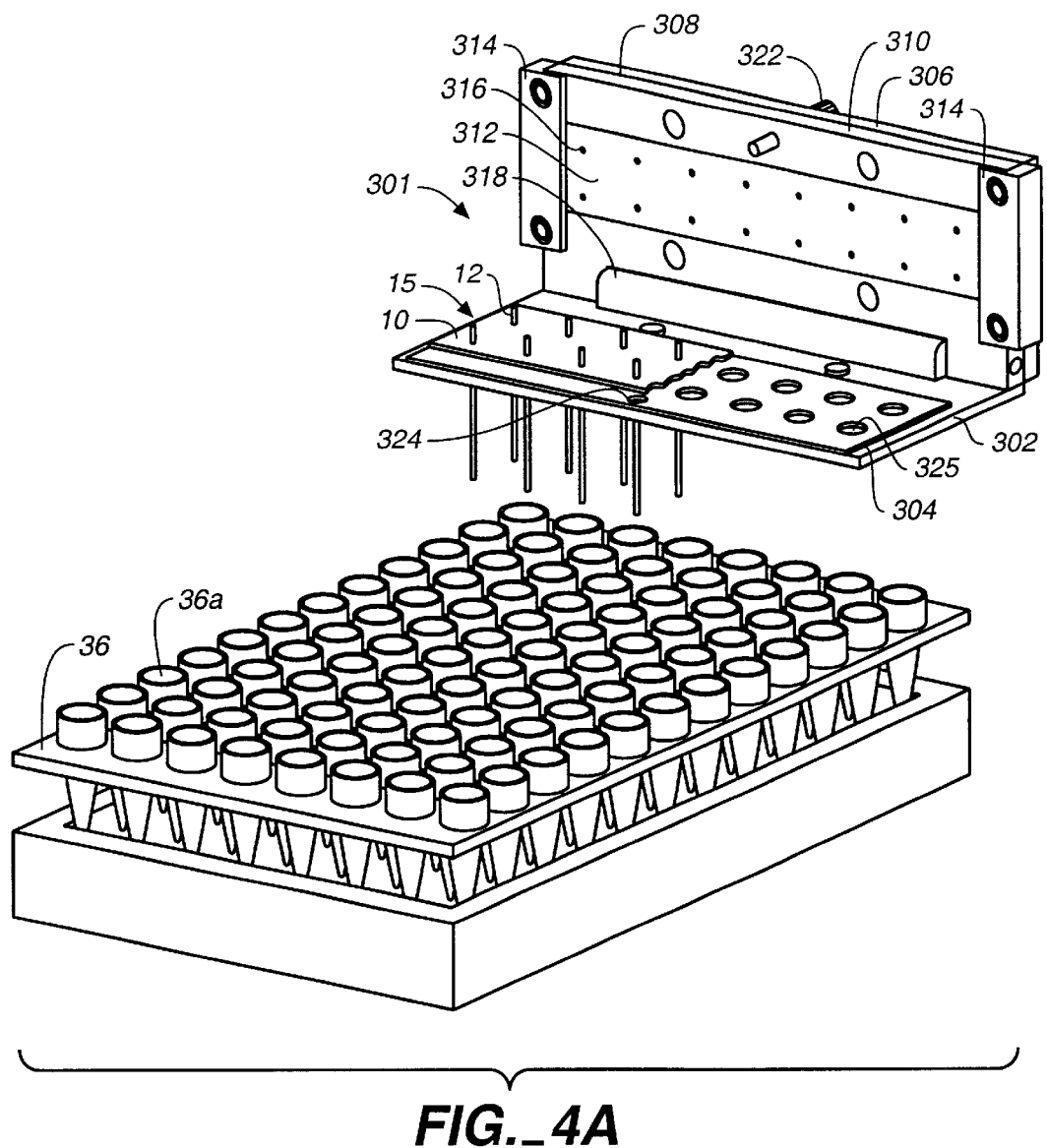
FIG._4A

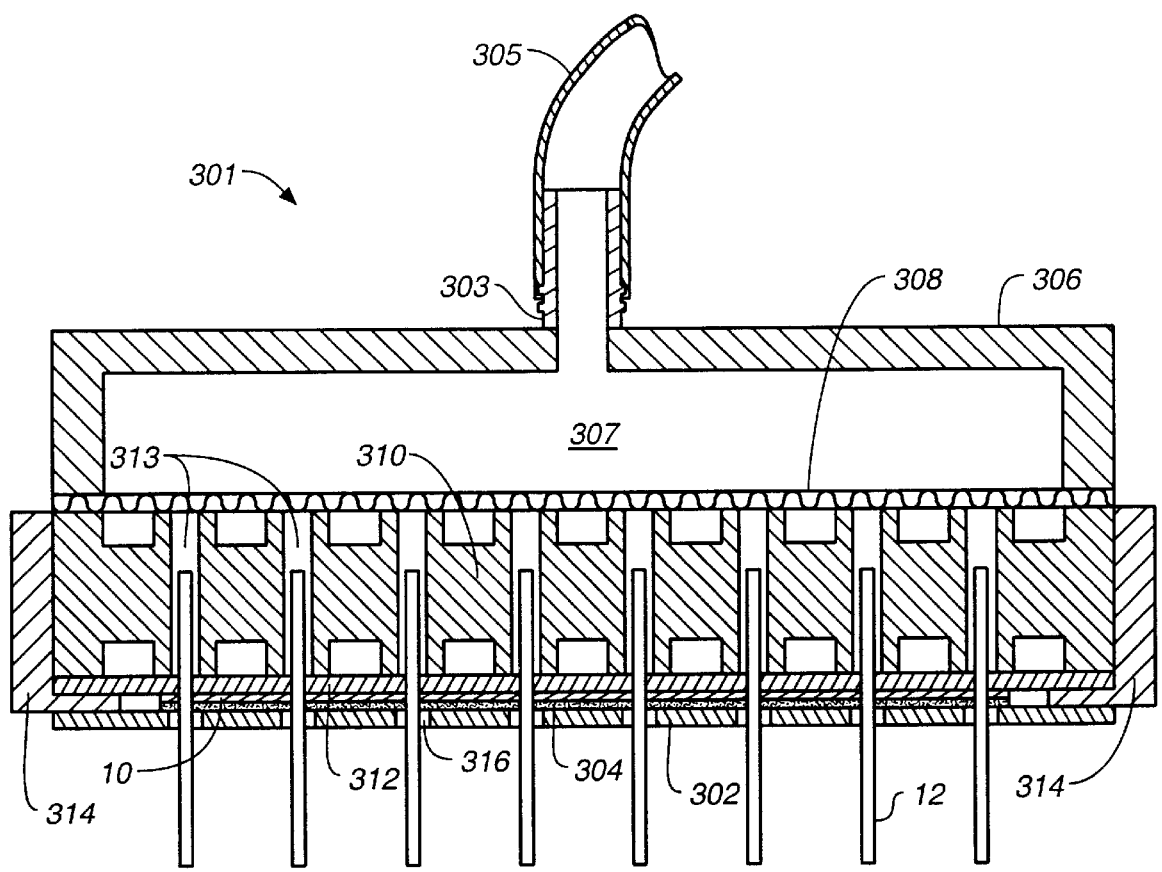
FIG._4B
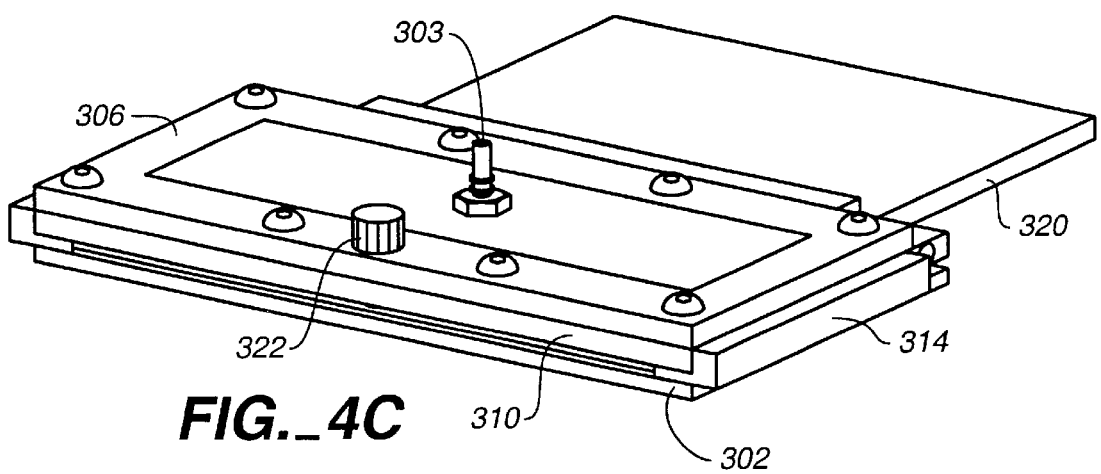
FIG._4C

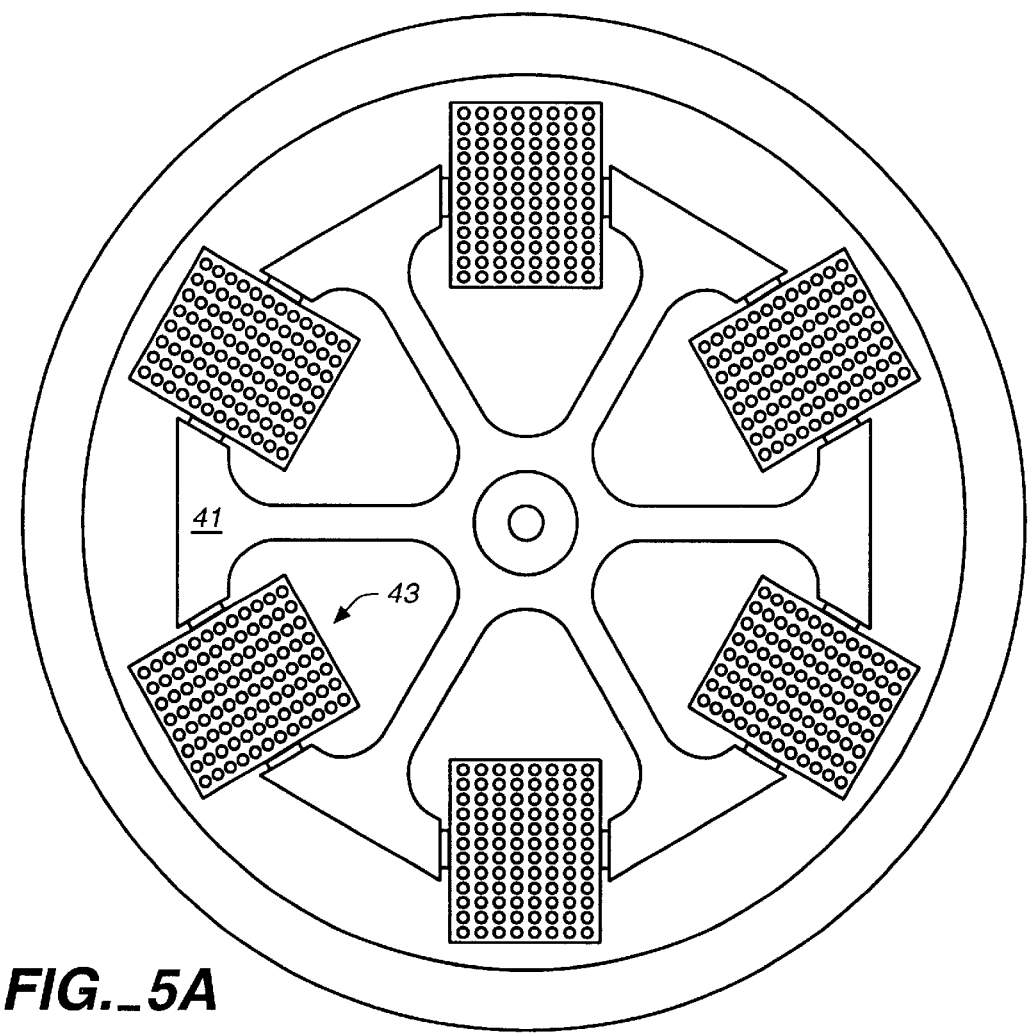
FIG._5A
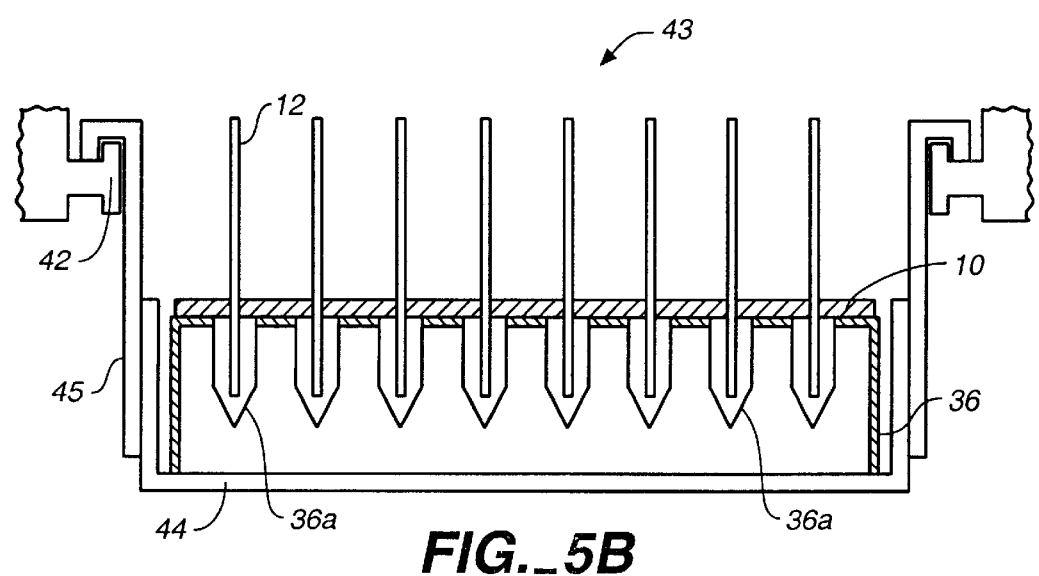
FIG._5B

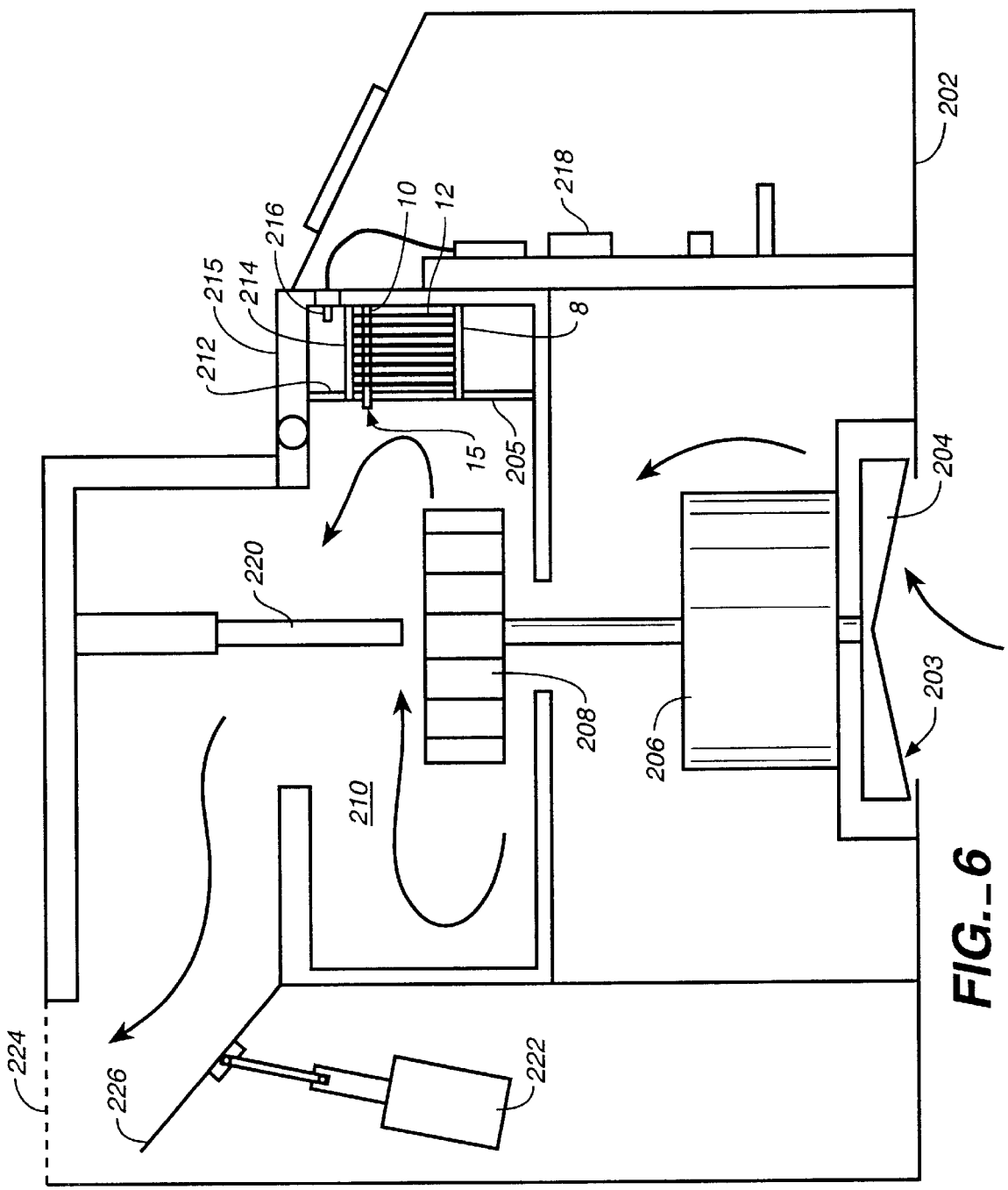
FIG._6

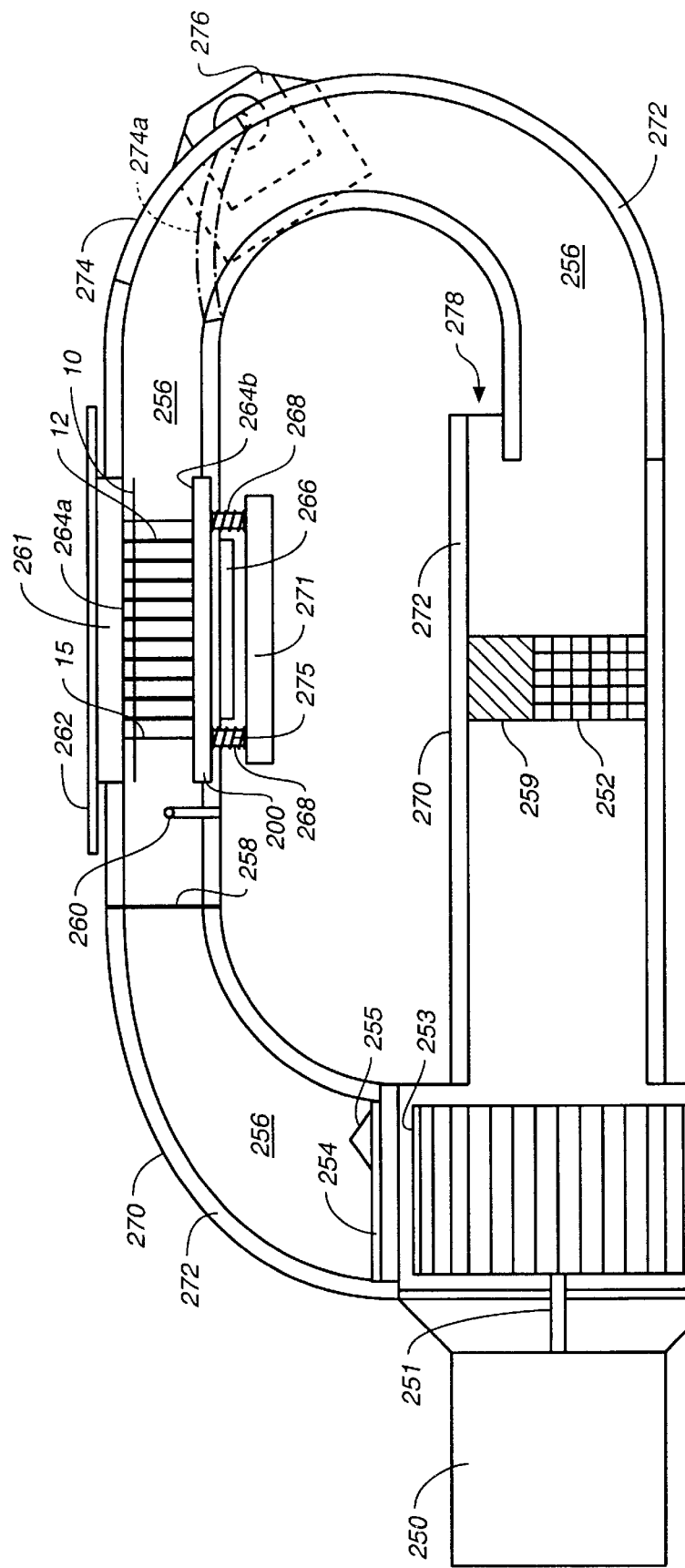
FIG._7A

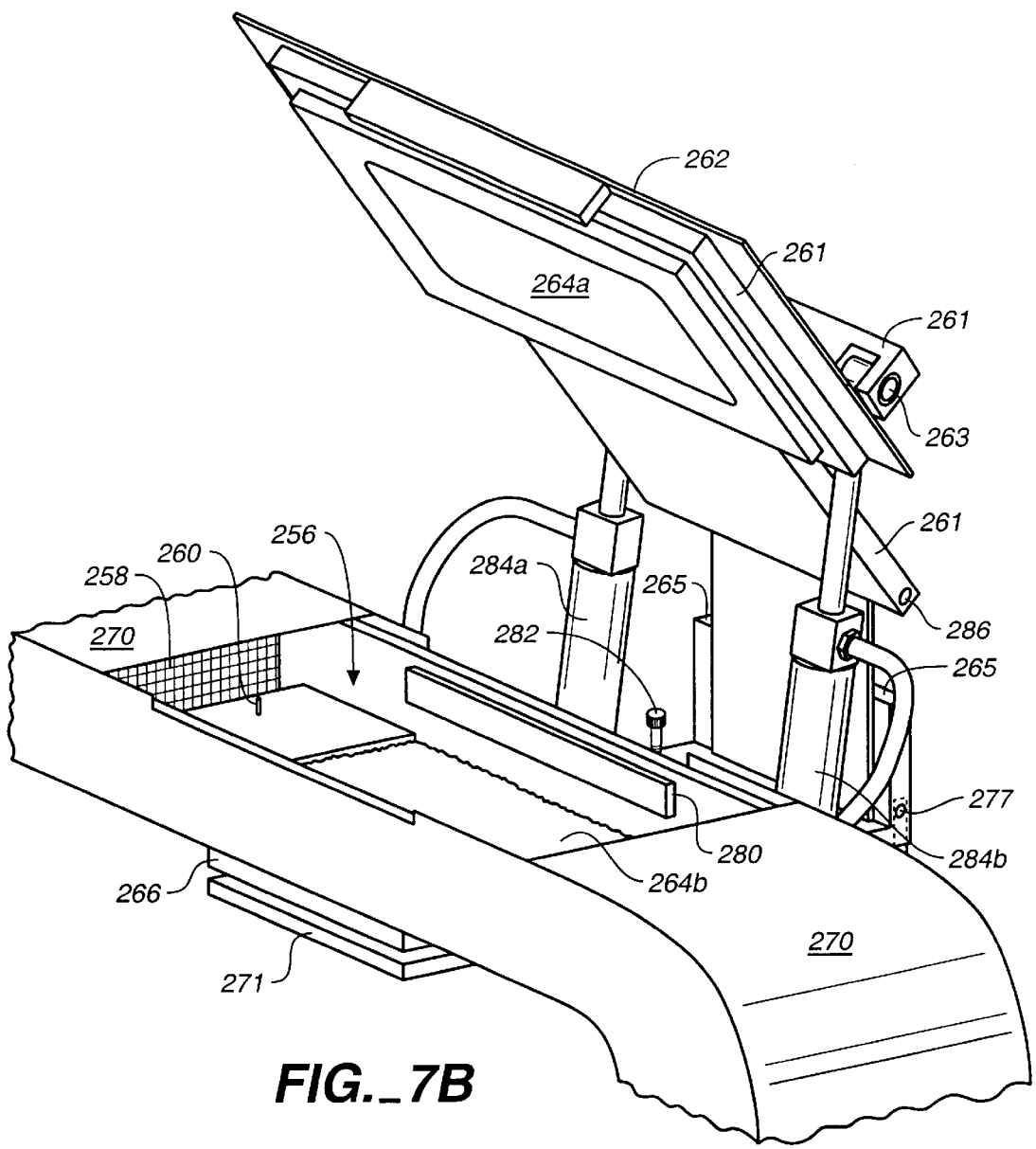
FIG._7B

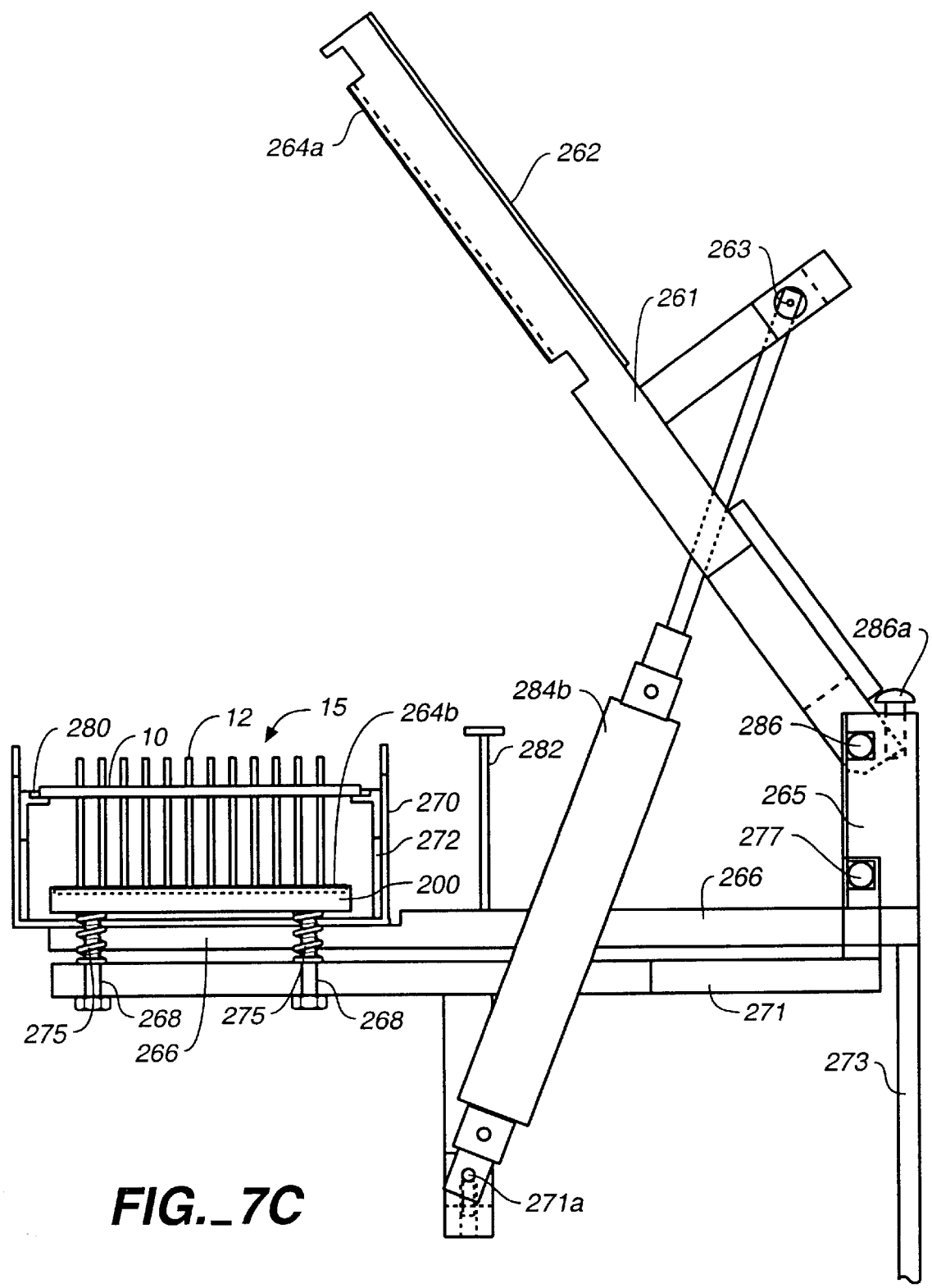
FIG._7C

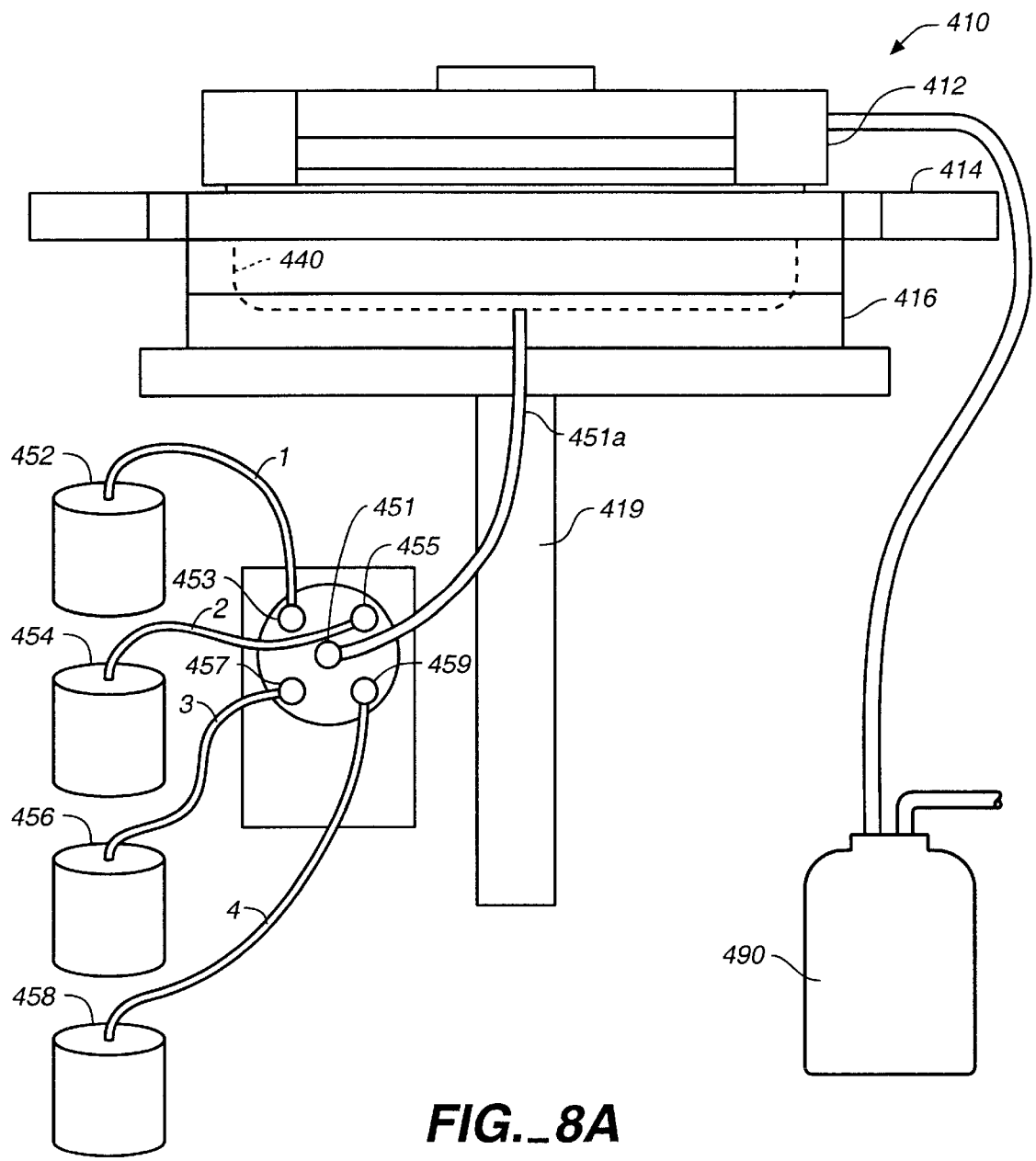
FIG._8A

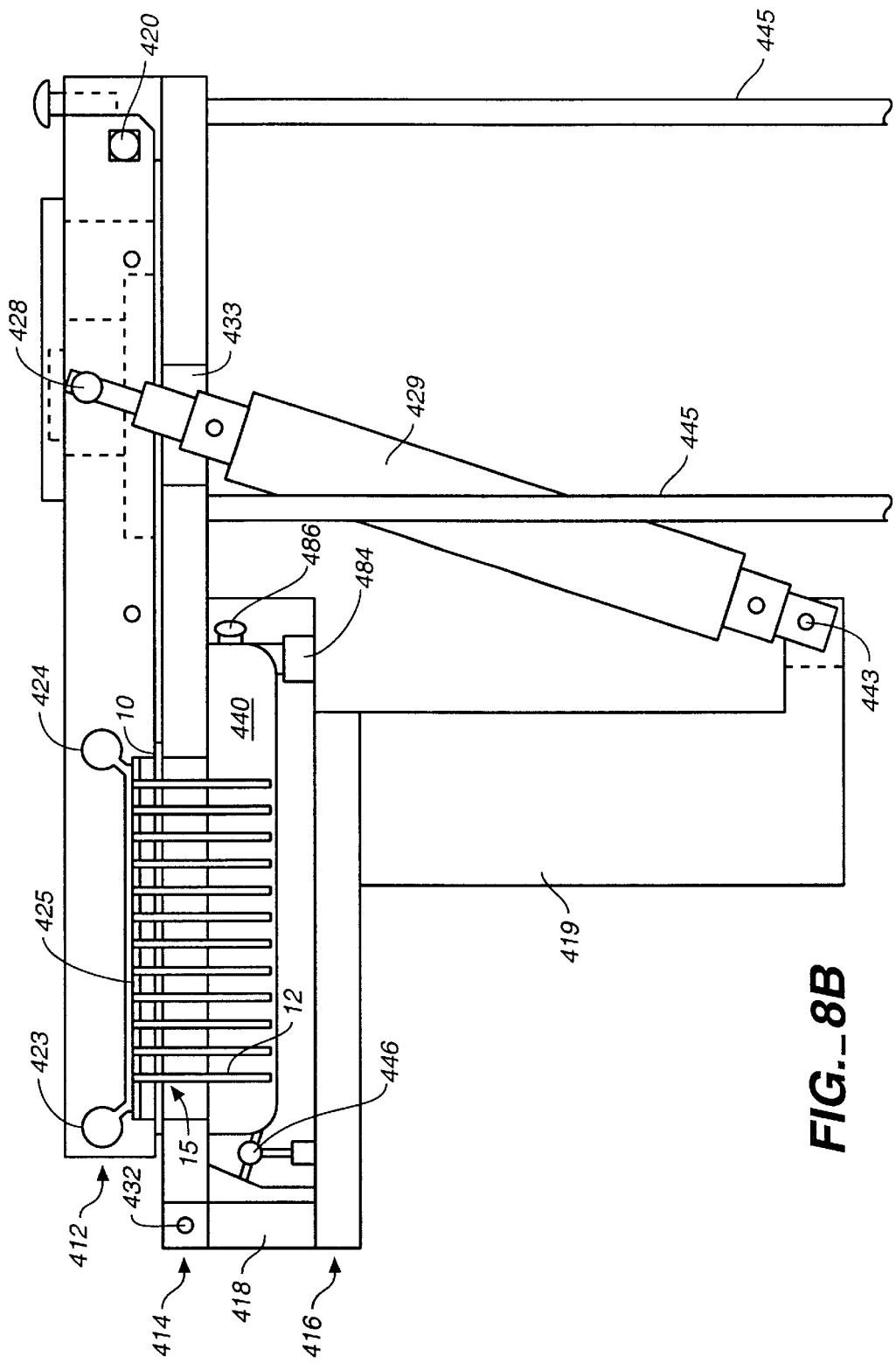
FIG._8B

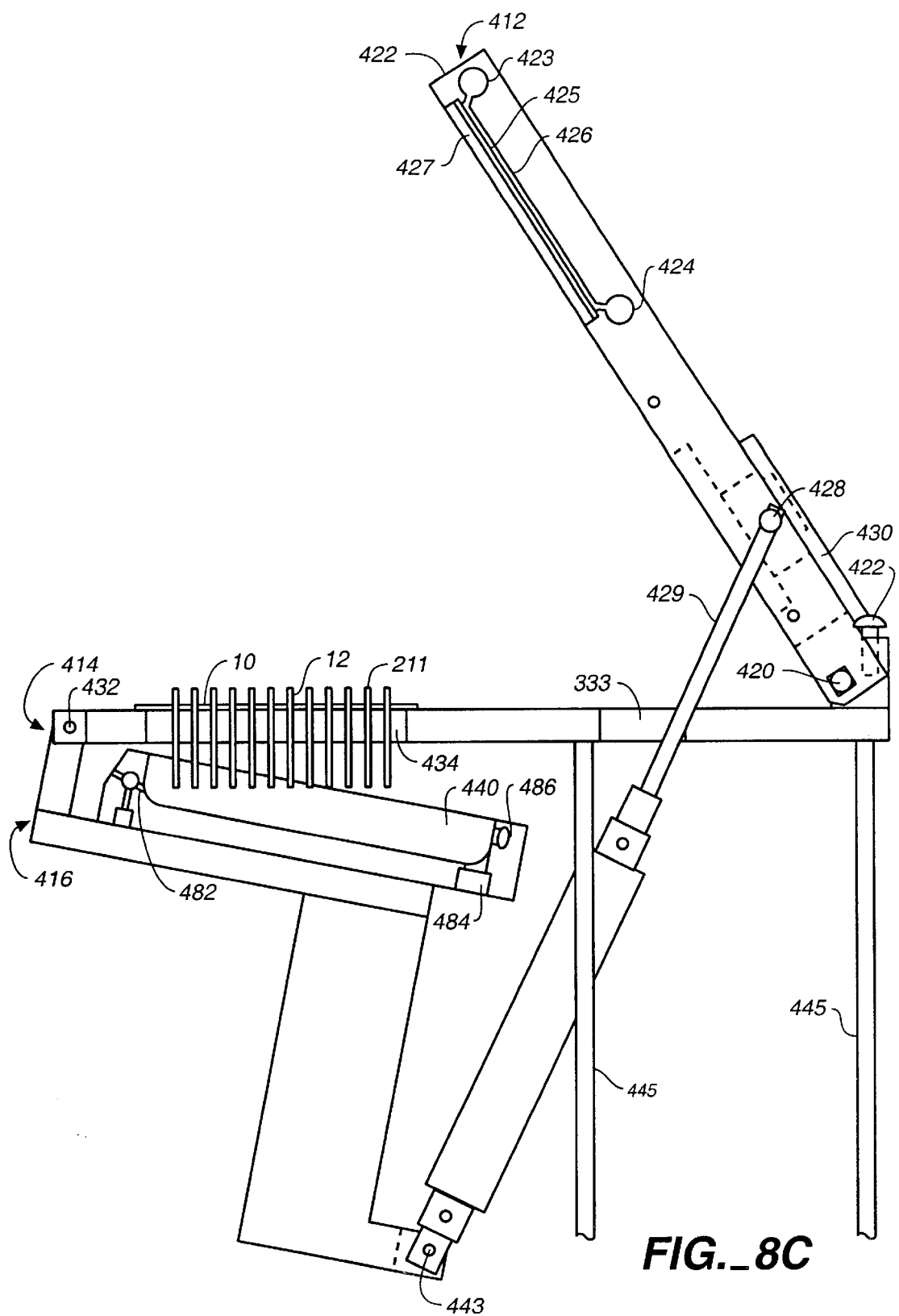
FIG._8C

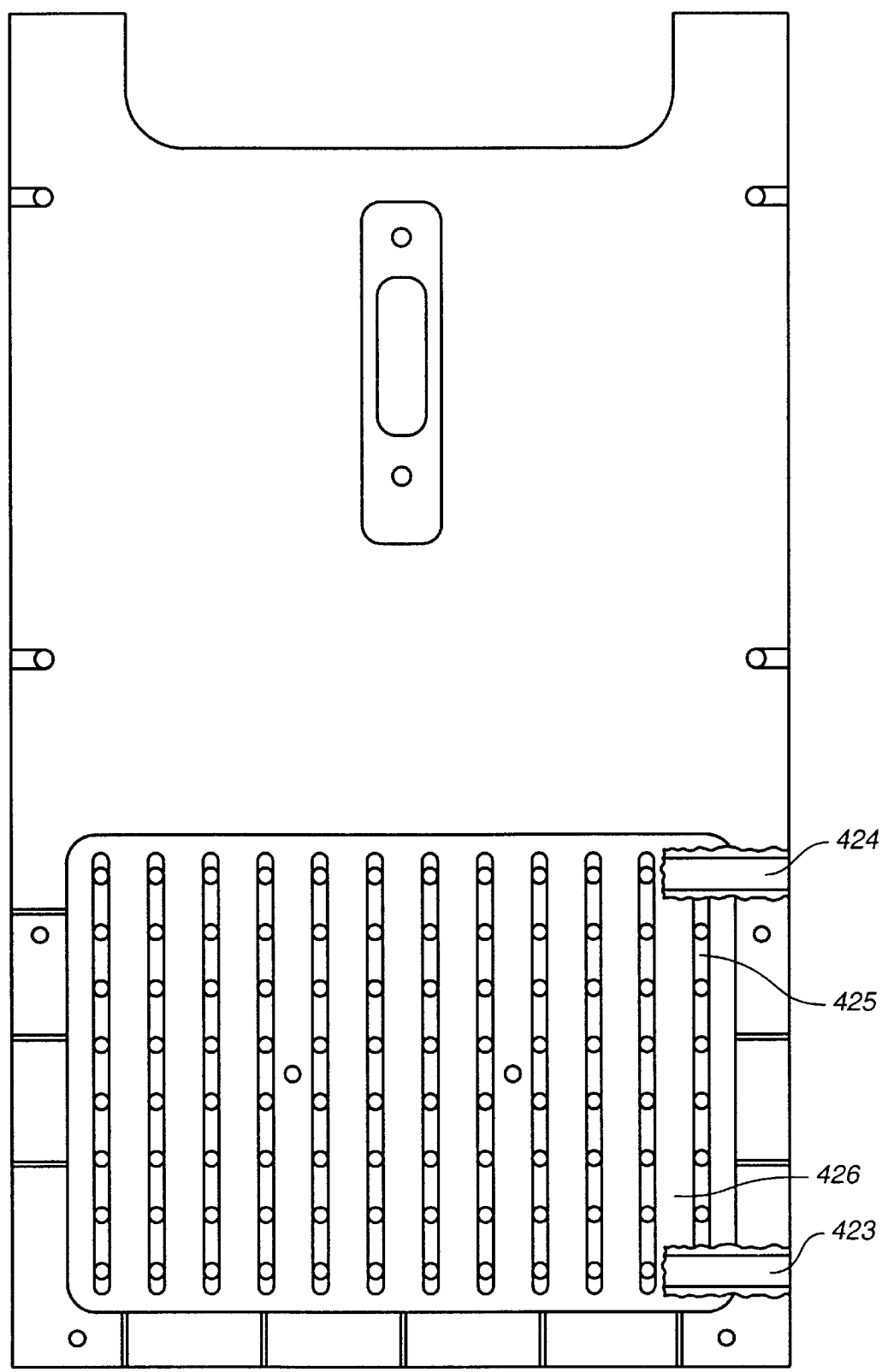
FIG._8D

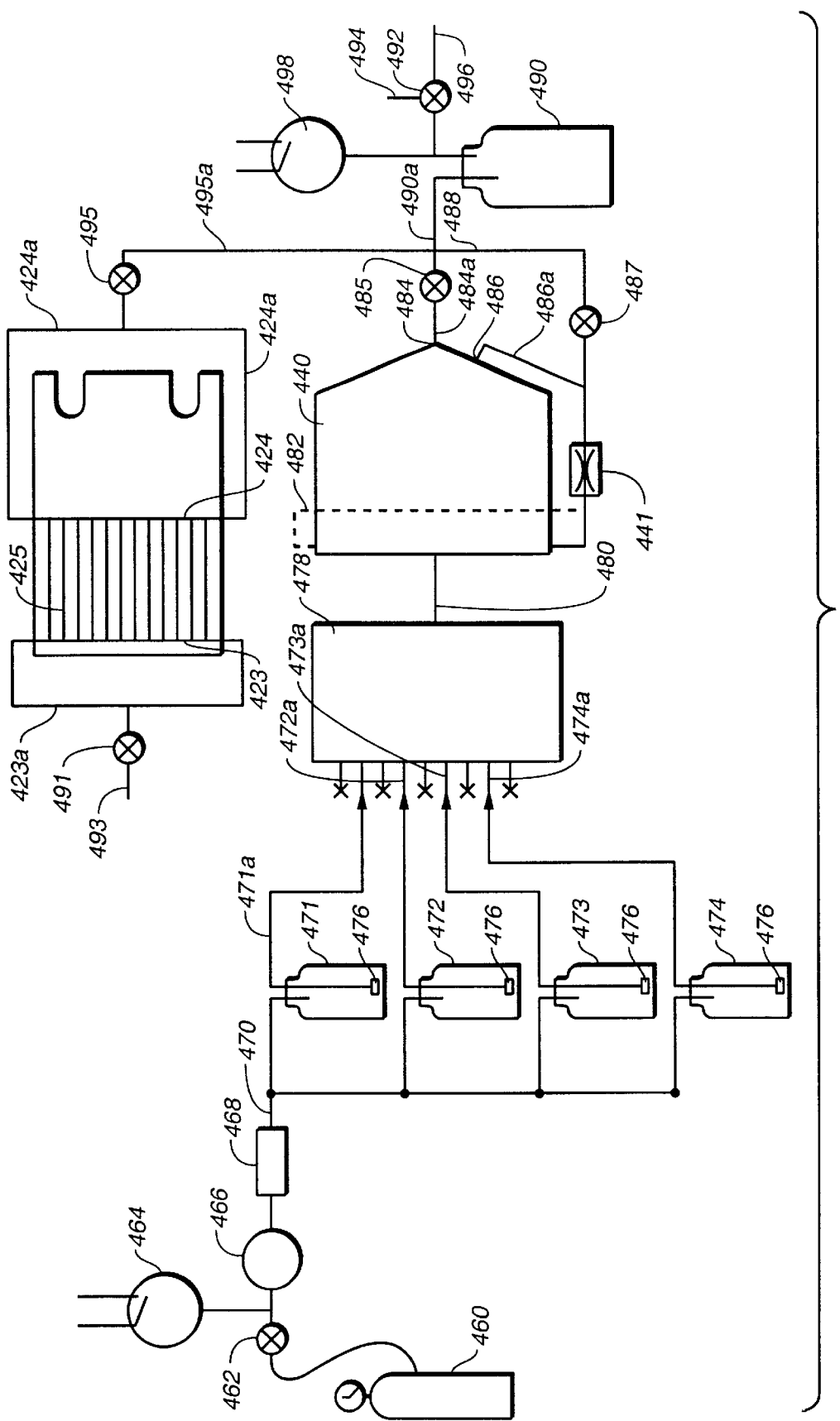
FIG._8E

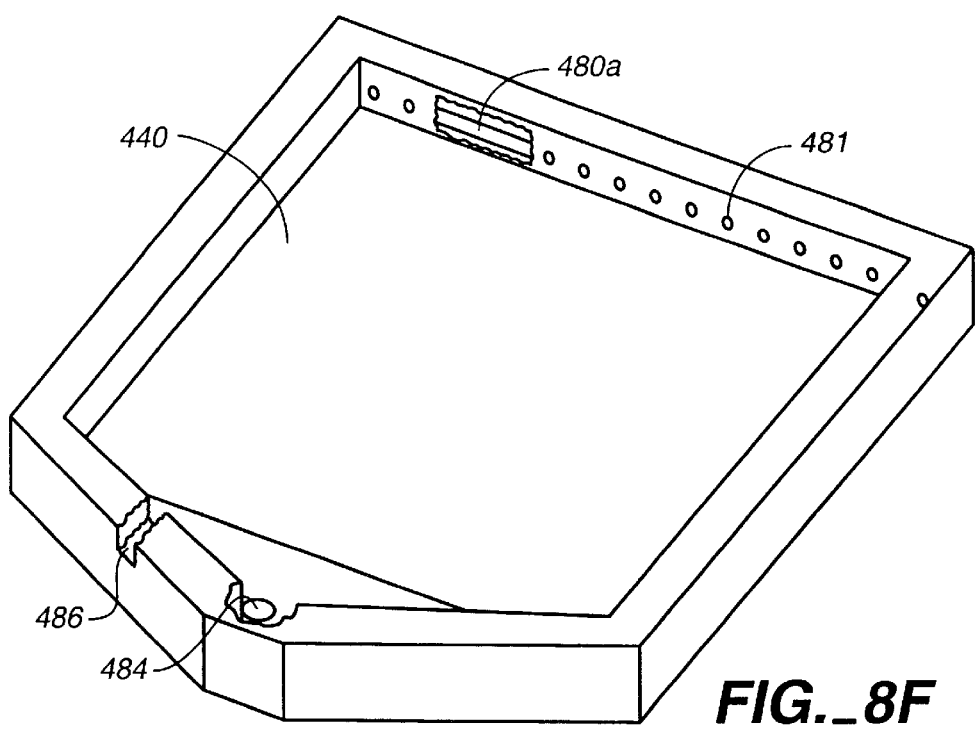
FIG._8F
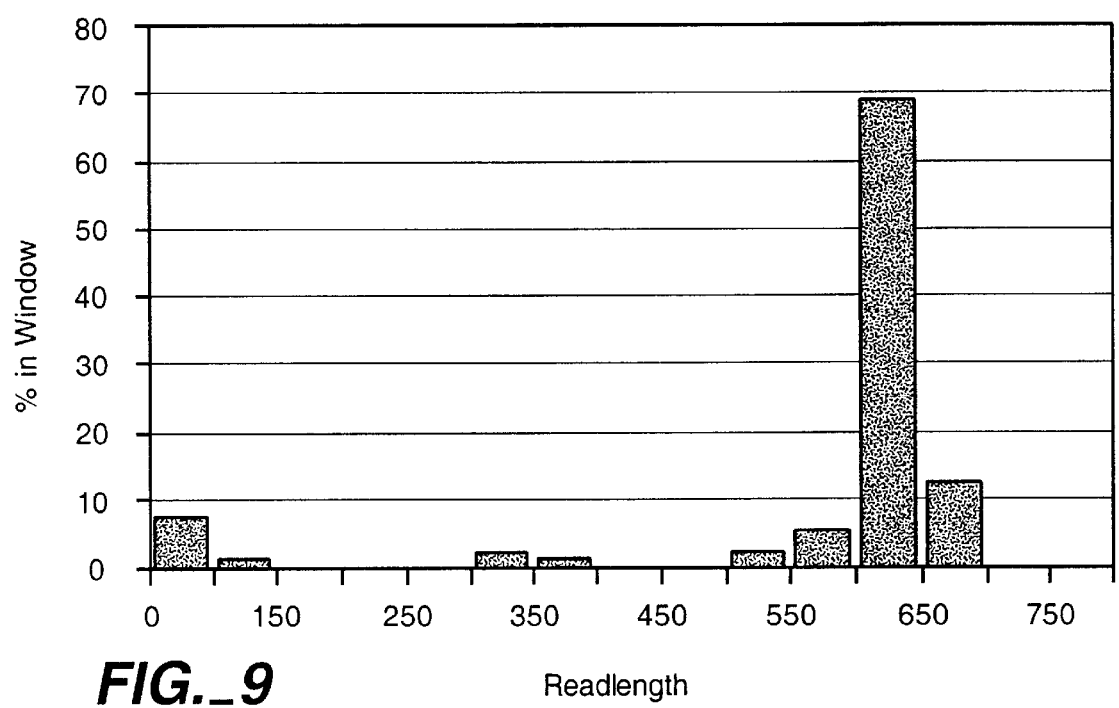
FIG._9

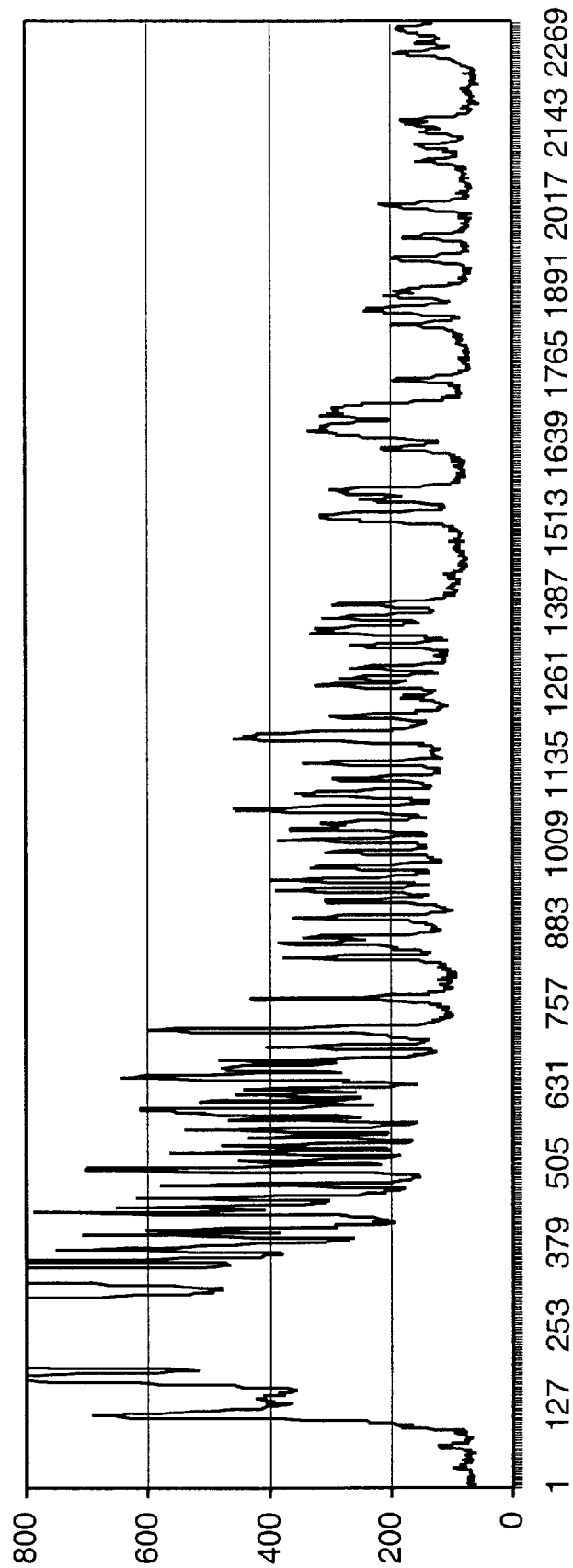
FIG._10

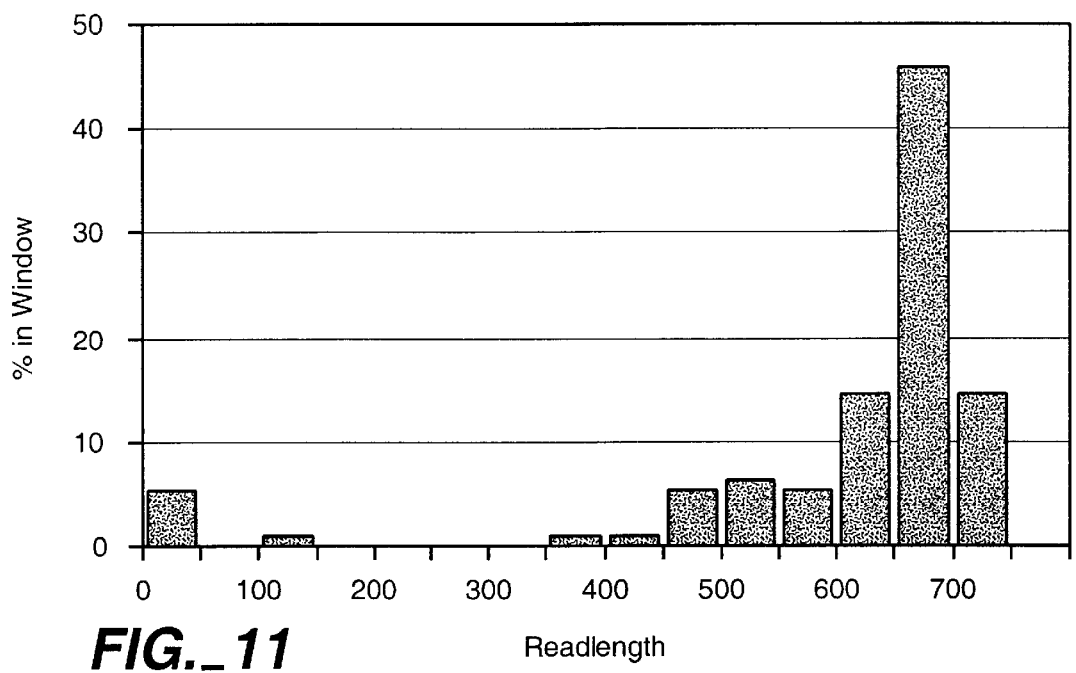
FIG._11
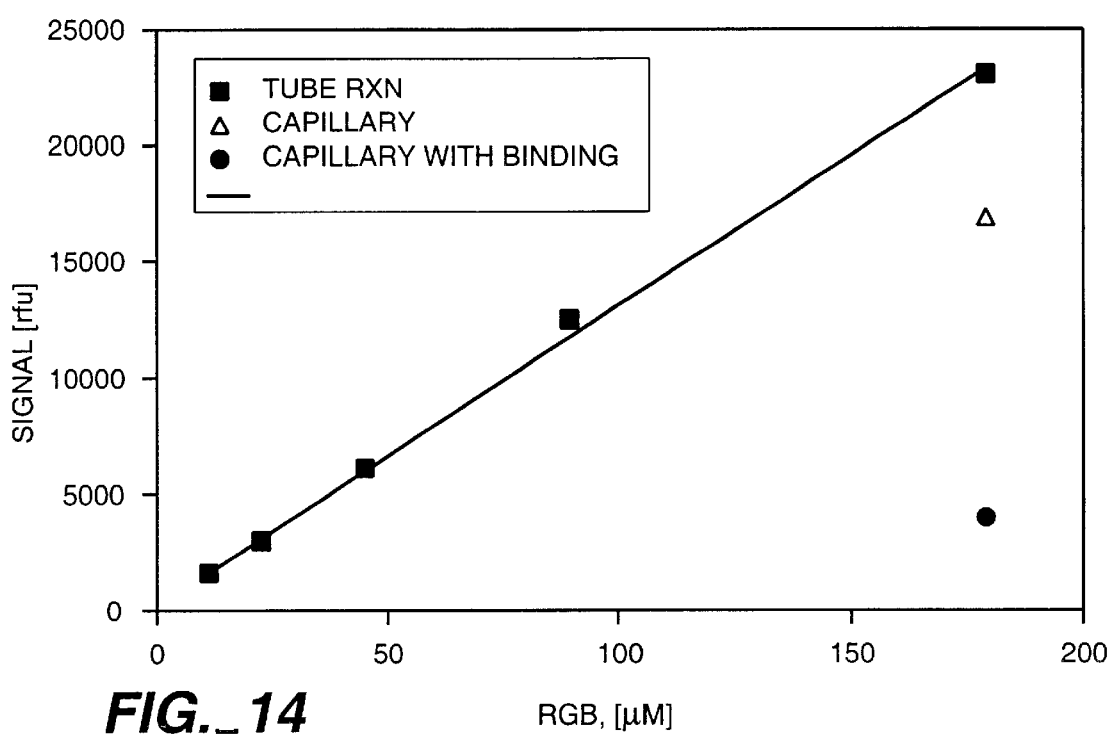
FIG._14

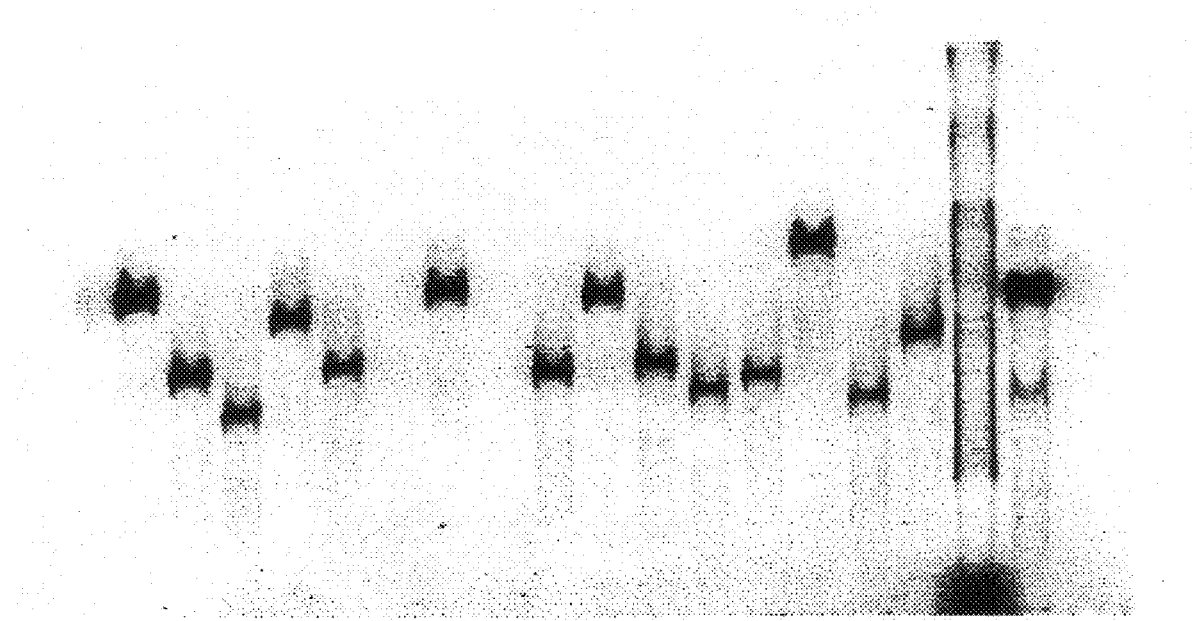
FIG._12A
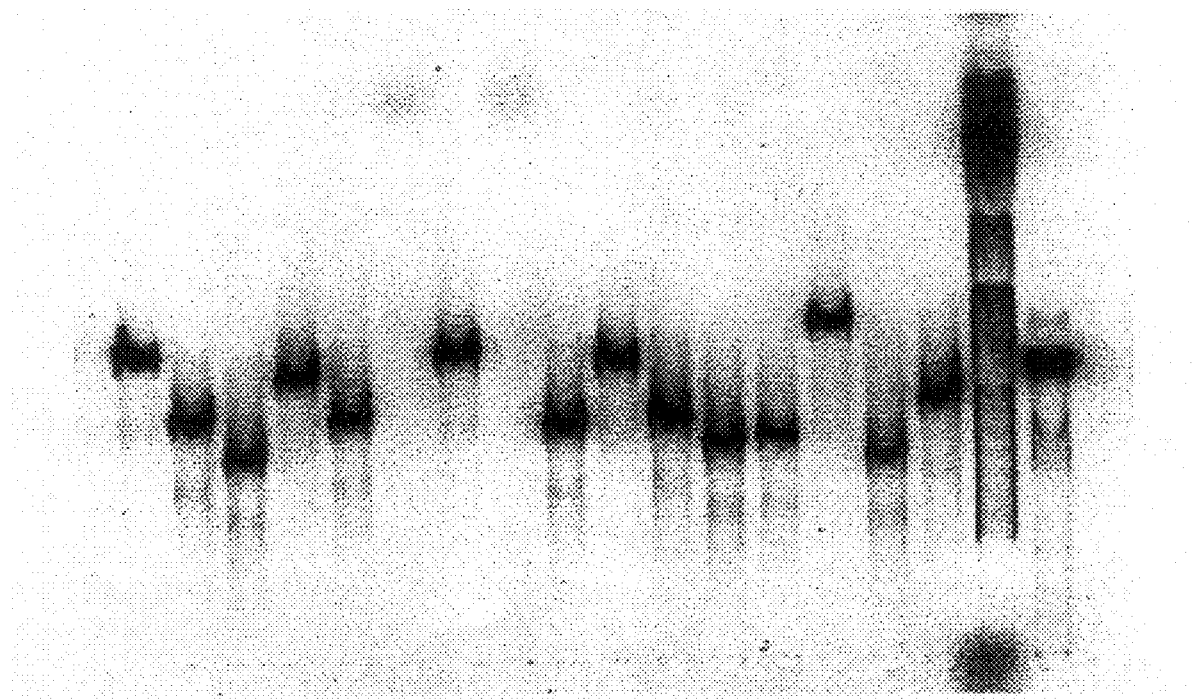
FIG._12B

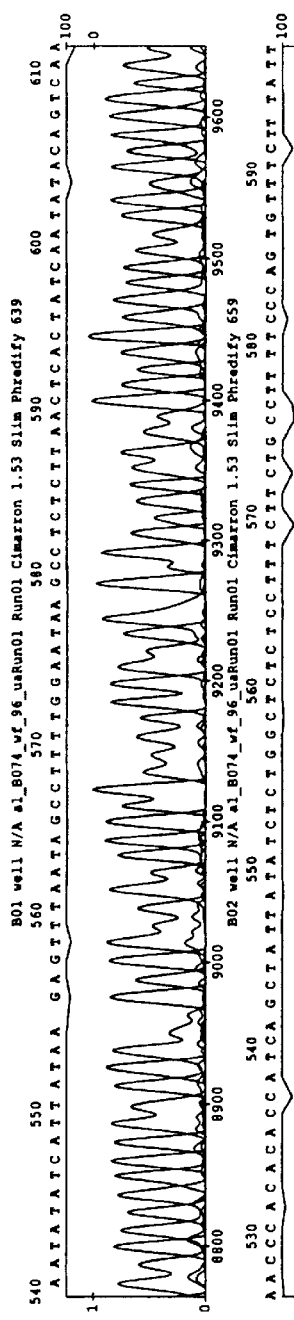
FIG._13A
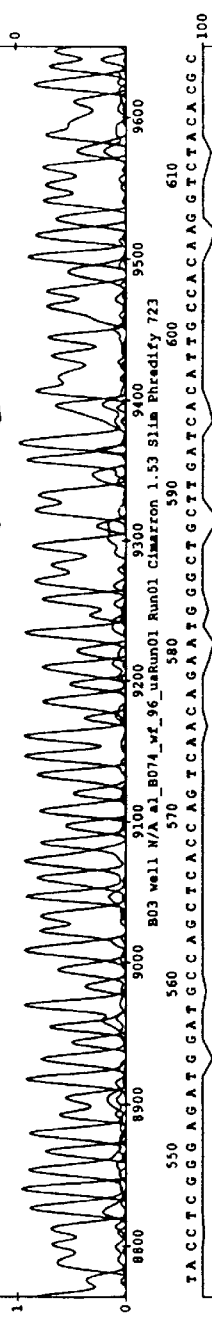
FIG._13B
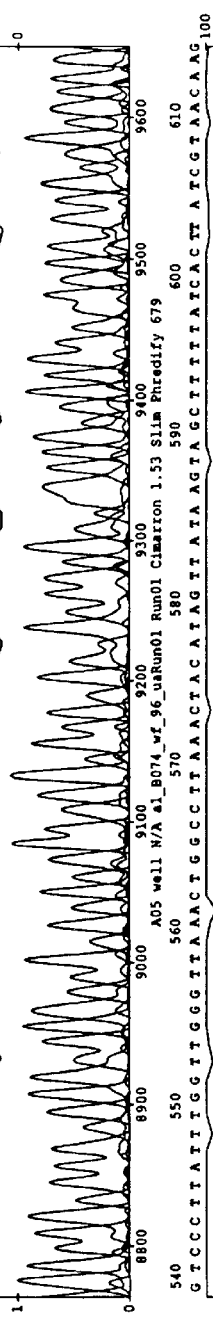
FIG._13C
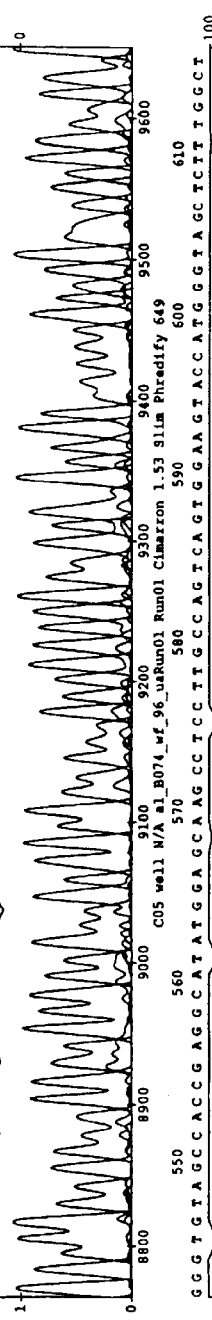
FIG._13D
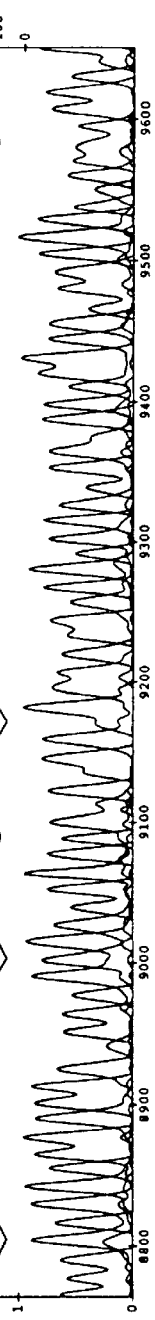
FIG._13E

LOW VOLUME CHEMICAL AND BIOCHEMICAL REACTION SYSTEM

CROSS-REFERENCE TO RELATED APPLICATION

This application claims priority from provisional application Ser. No. 60/146,732 filed Aug. 2, 1999.

TECHNICAL FIELD OF THE INVENTION

This invention relates to a method and apparatus for performing small scale reactions. In particular, the instant disclosure pertains to small scale cycling reactions, isothermal reactions, and devices for assembly of sub-microliter reaction mixtures.

BACKGROUND OF THE INVENTION

The Human Genome Program is a scientific endeavor that is a national priority of the United States. The original goal of the federally funded U.S. effort had been to complete the sequence at ten-fold coverage by the year 2005. A draft five-fold deep version of the human genome will now be produced by the year 2001. To accomplish this goal, the effort has accelerated to improve sequencing throughput rates and reduce DNA sequencing costs.

In the late 1970s, Sanger et al. developed an enzymatic chain termination method for DNA sequence analysis that produces a nested set of DNA fragments with a common starting point and random terminations at every nucleotide throughout the sequence. Lloyd Smith, Lee Hood, and others modified the Sanger method to use four fluorescent labels in sequencing reactions enabling single lane separations. This resulted in the creation of the first automated DNA sequencers that used polyacrylamide slab gels. More recently, fluorescent energy-transfer dyes have been used to make dye sets that enhance signals by 2- to 10-fold and simplify the optical configuration.

Automated fluorescent capillary array electrophoresis (CAE) DNA sequencers appear to be the consensus technology to replace slab gels. Capillary gel electrophoresis speeds up the separation of sequencing products and has the potential to dramatically decrease sample volume requirements. The 96-channel CAE instrument, MegaBACE™, which is commercially available from Molecular Dynamics (Sunnyvale, Calif.), uses a laser-induced fluorescence (LIF) confocal fluorescence scanner to detect up to an average of about 625 bases per capillary (Phred 20 window) in 90 minute runs with cycle times of two hours. Confocal spatial filtering results in a higher signal-to-noise ratio because superfluous reflections and fluorescence from surrounding materials are eliminated before signal detection at the photomultiplier tube (PMT). Accordingly, sensitivity at the level of subattomoles per sequencing band is attainable. Confocal imaging is also particularly important in capillary electrophoresis in microchip analysis systems where the background fluorescence of a glass or plastic microchip may be much higher than that of fused silica capillaries. Capillary array electrophoresis systems will solve many of the initial throughput needs of the genomic community for DNA analysis. However, low volume sample preparation still presents a significant opportunity to increase throughput and reduce cost.

While fluorescent DNA sequencers are improving the throughput of DNA sequence acquisition, they have also moved the throughput bottleneck from sequence acquisition back towards sample preparation. In response, rapid methods for preparing sequencing templates and for transposon-facilitated DNA sequencing have been developed as have magnetic bead capture methods that eliminate centrifugation. Thermophilic Archae DNA polymerases have been screened and genetically engineered to improve fidelity, ensure stability at high temperatures, extend lengths, and alter affinities for dideoxynucleotides and fluorescent analogs. These improvements have resulted in lower reagent costs, simpler sample preparation, higher data accuracy, and increased readlengths.

The sequencing community has also developed higher throughput methods for preparing DNA templates, polymerase chain reaction (PCR) reactions, and DNA sequencing reactions. Sample preparation has been increasingly multiplexed and automated using 96- and 384-well microtiter plates, multi-channel pipettors, and laboratory robotic workstations. In general, these workstations mimic the manipulations that a technician would perform and have minimum working volumes of about a microliter, although stand-alone multi-channel pipettors are being used to manipulate smaller volumes.

A typical full-scale sample preparation method for DNA shotgun sequencing on capillary systems begins by lysing phage plaques or bacterial colonies to isolate subcloned DNA. Because capillary electrophoresis is more sensitive to impurities in sequencing reactions than slab gels, the subcloned DNA insert is frequently PCR-amplified to exponentially increase its concentration in the sample. Next, exonuclease I (ExoI) and arctic shrimp alkaline phosphatase (SAP) are added to perform an enzymatic cleanup reaction to remove primer and excess dNTPs that interfere with cycle sequencing. ExoI is used to degrade the single-stranded primers to dNMPs without digesting double-stranded products. SAP converts dNTPs to dNMPs and reduces the DNTP concentration from 200 $\mu$M, as used for the PCR reaction, to less than 0.1 $\mu$M for use with fluorescent sequencing. The reaction is performed at 37° C. and then heated to 65° C. to irreversibly denature the ExoI and SAP.

Because the PCR amplification produces excess template DNA for cycle sequencing, the ExoI/SAP treated PCR sample can be diluted five-fold before cycle sequencing. This reduces the concentration of contaminants into a range that causes less interference with CAE analysis. Cycle sequencing reagents are added, typically with fluorescently labeled dye primers or terminators and the reaction is thermal cycled to drive linear amplification of labeled fragments. Finally, after cycling, the samples are ethanol precipitated, resuspended in formamide, another denaturant, or water, and the sample is electrokinetically injected into the CAE system.

This workflow has resulted in a dramatic improvement in the performance of the MegaBACE system and similar workflows currently appear to be the methods of choice for other CAE systems as well. Using actual samples from single plaques and colonies of human genomic random subclones or Expressed Sequence Tags (ESTs), this workflow with linear polyacrylamide as a separation matrix has improved the success rate of samples over 200 base pairs from about 60% to 85–90%, and has improved the average readlength from about 400 to greater than 600 bases. Furthermore, this method has proven to be quite robust.

While the above sample preparation methods have greatly increased throughput, the cost of reagents remains a major component of the cost of sequencing. CAE requires only subattomoles of sample, but presently samples are prepared in the picomole range. Reducing the reaction volume will therefore reduce the cost of DNA sequencing and still provide enough material for analysis. However, substantial reductions in reaction volume can only be achieved if satisfactory methods can be developed for manipulating and reacting samples and reagents. Ideally, such a method would be automated and configured in order that multiple samples could be produced at one time. Moreover, it would be desirable to integrate such a method as a module capable of interfacing with additional components, such as CAE and a detector for separation and analysis.

Several devices have been designed to aid in the automation of sample preparation. For example, U.S. Pat. No. 5,720,923 describes a system in which small scale cycling reactions take place in tubes with diameters as small as 1 mm. The tubes are subsequently exposed to thermal cycles produced by thermal blocks to effect the desired reaction. Multiple samples may be processed in a single tube by drawing in small amounts of sample, each of which are separated in the tube by a liquid which will not combine with the sample. Fluid moves through the tubes by means of a pump. These features are incorporated into a system which automatically cleans the tubes, moves sample trays having sample containing wells, and brings the tubes into contact with the wells in the sample trays.

U.S. Pat. No. 5,785,926 discloses a system for transporting small volumes of sample. In this system, at least one capillary tube is used to transport small amounts of sample. A precision linear actuator connected to a computer controlled motor acts as a pneumatic piston to aliquot and dispense liquid using the tube. The sample amount is monitored by an optical sensor that detects the presence of liquid within the capillary segment. The system includes a fluid station containing liquids to be deposited and a positioning device for positioning the transport capillary.

U.S. Pat. No. 5,897,842 discloses a system for automated sample preparation using thermal cycling. In this system a reaction mixture is pumped into a capillary tube. One end of the tube is sealed using pressure from an associated pump while the other end is sealed by pressing the tube against a barrier. The pump also serves to move fluid within the tube. Once the ends are sealed, the tube is exposed to thermal cycles. In this system a robotic transfer device moves the tubes between the sample preparation station where the pump loads the components of the reaction mixture into the tubes and the thermal cycling station.

There is an additional need for an automated system that is able to perform small-scale thermal cycling reactions in a highly parallel manner. The system should allow for rapid preparation of cycling reactions with minimal consumption of reagents. The combination of reducing the amount of reagents required for a reaction and reducing the time required for a reaction will greatly reduce the overall cost of preparation of cycling reactions.

Capillary array electrophoresis systems and capillary electrophoresis microchip analytical systems can detect sub-attomoles of reaction products. It is one object of the invention to disclose a method and system for cycling reactions that operate on a submicroliter scale that takes advantage of the high sensitivity of these analytical systems. This reduction of reaction volume will lower the reagent requirements and cost of each reaction. It is a further object to provide an automated system that is able to reduce the time required for cycling reaction preparation. It is an additional object of the invention to provide a system that may be integrated with analytical instruments including capillary array electrophoresis systems and electrophoresis chips.

It is a further object of the invention to provide an automated system for preparing reactions and filling reaction containers using capillary action. This allows metering a quantity of liquid into a capillary tube length of fixed volume without using external force to pump liquids. It is a further object to disclose a reagent-metering device that also may act as the reaction container. It is also an object of the invention to provide a system that allows the nanoscale reaction containers to be cleaned and reused, saving material costs.

It is a further object of the invention to provide a system with highly parallel processing, allowing greater throughput. Preferably, the system would match the density of microwell plates. It is also an object of the invention to have an automated system in which a number of different cycling reactions could be performed in parallel using a single temperature regulation source, allowing more efficient use of the thermal cycling apparatus. It is a further object to perform isothermal reactions in a highly parallel manner in submicroliter volumes. It is also an object of the invention to provide an automated reaction preparation system that is able to utilize available automation tools by being compatible with standard plate size formats.

SUMMARY OF THE INVENTION

The above objects have been achieved through a system and method for preparing cycling reaction mixtures. The system uses a capillary cassette comprised of a number of capillary tube segments arranged in parallel alignment. The tube segments extend through a substrate and are generally positioned with uniform spacing. The capillary cassette may be used both to meter reagents and as a reaction chamber in which the reaction is conducted.

A reaction mixture containing a nucleic acid sample and reaction reagents for performing a thermal cycling reaction (such as the polymerase chain reaction, ligase chain reaction, or chain termination sequencing reaction) is introduced into the capillaries of a capillary cassette. In one embodiment each capillary contains a unique nucleic acid sample but the same reaction reagents.

The reaction mixture may be generated in various manners. In one sample preparation method, sample DNA adheres to the interior of the capillary tubes of the capillary cassette or onto a substrate. The liquid in which the DNA was suspended may be eliminated from the capillary or substrate while the nucleic acid is retained, bound to the capillary or substrate. The reaction reagents may then be introduced into the capillary or substrate, combining the sample and reaction reagents to form an assay mixture. In another sample preparation method, the capillaries in a capillary cassette or the wells in a multiwell plate are coated with dehydrated reaction reagents. The nucleic acid sample is introduced into the capillaries of the capillary cassette or the wells of a multiwell plate and the nucleic acid sample rehydrates the reaction reagents to form a reaction mixture. If the multiwell plate is used, the reaction mixture is subsequently transferred into the capillaries of a capillary cassette. In another sample preparation method, both the reaction reagents and the nucleic acid samples are metered by the capillaries of a capillary cassette. The capillaries are dipped into the wells of a sample plate and a fixed amount of fluid (defined by the interior volume of the capillary) is drawn into the capillary. The volume of liquid metered by the capillary tubes is dispensed by positive displacement, centrifugal force, or other displacement method into the wells of a microplate. A capillary cassette is used to meter both the reaction reagents in a similar manner and dispense the metered liquids onto a location on a substrate combining the sample and reaction reagents to form a reaction mixture. In any of these reaction mixture preparation methods, reaction reagents, nucleic acid samples and assembled reaction mixtures are introduced into the capillary tubes of a capillary cassette or drawn into the capillary cassette by capillary action. Liquids may also be introduced into the capillaries by active filling, such as by pressure or vacuum. For example, one end of the capillaries may be sealed with a liquid impermeable (hydrophobic), gas permeable membrane. By applying a vacuum force to one side of the membrane, the capillary will fill with liquid to the level of the membrane, where hydrophobic forces will prevent further filling of the capillary.

The capillary cassette filled with the reaction mixture is next sealed by pressing the two ends of the capillary tube segments against deformable membranes. The capillary cassette with ends sealed against deformable membranes is contained within an interior chamber of a temperature cycling device. The temperature cycling device exposes the contents of the capillaries to thermal cycles, causing the thermal cycling reaction to occur. In one embodiment the thermal cycling apparatus is an air thermal cycling device. This device receives the capillary cassette into an interior chamber where the ends of the capillaries in the cassette are sealed. The temperature changes occur using rapidly flowing air. The temperature of the cycling air may be rapidly lowered by venting air to outside the interior cycling chamber. A thermocouple sensor in the air path of the capillary cassette allows for precise monitoring of the temperature of the reaction mixture. Given the rapid transfer of heat through the capillary and precise temperature sensing allowed by the thermocouple, rapid reaction times are possible. The complete thermal cycling times needed for 30 cycles of denaturing heating followed by a period of lower temperature for extension of a 600–700 base DNA strand can be performed in 30 minutes or less and could theoretically be effected in as little as 8 minutes. Following a programmed number of thermal cycles, the capillary cassette is removed from the temperature cycling chamber.

The reaction mixture is next dispensed from the capillary cassette and transferred into a substrate. In one embodiment the substrate into which the completed reaction mixture is dispensed is an analytical chip, such as an electrophoresis chip. Following transfer from the capillary cassette, the reaction mixture may be separated and analyzed. Alternatively, the sample may be dispensed into a microplate or other substrate. The substrate may then be placed, manually or by an automated system, in a location where it may be analyzed by capillary array electrophoresis. In addition to electrophoresis, the instant reaction preparation system may also be adapted for use in preparing nucleic acid, protein or other biomolecules for microarray analysis, mass spectrometry analysis, or other analysis methods. The capillary cassette may also be used for conducting ELISA or other assays requiring binding to a substrate.

The use of the present system allows a simplified transition between nanoscale and larger scale preparation steps. For example, the PCR step may be performed in the nanoscale in the capillary cassette of the present invention. The resulting products can be dispensed into a microplate well for enzymatic clean up on a larger scale such as microliter volumes. Following clean up, the amplified nucleic acid can again be metered into a nanoscale capillary cassette for subsequent reaction mixture preparation (e.g. cycle sequencing). This achieves a simple transition method from the nanoscales into larger scales.

Depositing the reaction mixtures from the capillary cassette into the wells of a 96 well plate allows subsequent analysis by the capillary array electrophoresis systems. Post reaction processing is also possible. This could include depositing the reaction mixture into ethanol to precipitate the DNA fragments produced in the reaction or dispensing the reaction mixture into formamide to denature double stranded DNA reaction products.

Following each use, the capillary cassette may be placed into a capillary cassette washer and washed. Following washing, the capillary cassette may be reused.

The system can be designed with magazines for holding the sample plates, the multi-well mixing plates, and the plates containing the finished reactions. This would allow the system to operate continuously to prepare reaction mixtures. In addition, an integrated system with a central electronic control would allow for a system that may simultaneously assemble reaction mixtures, perform thermal cycling or other reactions, and wash capillary cassettes.

The system is useful for the preparation of sequencing reactions, but may also be used in highly parallel preparation of cell lysates, plasmid extraction, polymerase chain reactions, ligase chain reactions, rolling circle amplification reactions, screening compound libraries for drug discovery or compound activity, protein digestion/sequencing, ELISA, radioimmunoassays and other chemical or biochemical reactions or assays.

BRIEF DESCRIPTION OF THE DRAWINGS

FIG. 1 is a schematic of an integrated system for the preparation of cycle sequencing reaction products.

FIG. 2 is a flow chart illustrating the steps in production of cycling reactions using the present system.

FIG. 3A is a perspective view of the capillary cassette of the present invention.

FIG. 3B is a perspective view of the capillary cassette inserted into a capillary cassette holder.

FIG. 3C is a flexible capillary cassette.

FIG. 3D illustrates the capillary cassette of FIG. 3C bent to a curved orientation such that the capillary ends are in a curved pattern.

FIG. 3E is a microchip device containing channels for sample preparation.

FIG. 4A illustrates a dispense head for dispensing liquid from the capillary cassette.

FIG. 4B shows an internal cross section of an air displacement dispense head of FIG. 4A.

FIG. 4C shows the dispense head of FIG. 4A with the dispense head closed.

FIG. 5A illustrates a top view of a centrifuge used to dispense fluid from the capillary cassette of FIG. 3A.

FIG. 5B illustrates a cross-section of a rotor arm of FIG. 5A holding a swinging microplate bucket containing a capillary cassette inserted into a microtiter plate.

FIG. 6 shows a schematic of an air-based thermal cycling device with the capillary cassette and holder shown in FIG. 3B inserted into the temperature cycling device.

FIG. 7A shows an internal cross section of an air-based thermal cycler with integrated capillary cassette sealing membranes.

FIG. 7B shows a detail of the air-based thermocycler of FIG. 7A, with the lid is raised to illustrate the chamber into which the capillary cassette is inserted.

FIG. 7C shows a cross section of the cassette compartment with the capillary cassette inserted into the internal chamber of the thermal cycler of FIG. 7A.

FIG. 8A is a front view of the capillary cassette wash station.

FIG. 8B is a side view of the view of FIG. 8A with the wash manifold lowered and the wash tank raised.

FIG. 8C is the view of FIG. 8B with the wash manifold raised and the wash tank lowered.

FIG. 8D is an interior cross-section of the wash manifold.

FIG. 8E is a schematic plumbing diagram of the wash station.

FIG. 8F is a top perspective view of the wash tank.

FIG. 9 shows a histogram of the percent success versus readlength window for the sequencing analysis of example 1.

FIG. 10 is an electropherogram of the reaction products of example 2.

FIG. 11 shows a histogram of the percent success versus readlength window for the sequencing analysis of example 3.

FIG. 12A shows a scanned gel image of electrophoretically separated PCR products prepared at full volume.

FIG. 12B show a scanned gel image of electrophoretically separated PCR products prepared at a nanoscale volume (500 nL).

FIGS. 13a–13e are electropherograms of analysis of sequencing mixtures prepared by performing PCR at 500 nL volumes, a cleanup reaction at full volumes, followed by cycle sequencing reactions performed at 500 nL.

FIG. 14 is a graph comparing signal strength of an isothermal reaction for products prepared in tubes, capillaries, and capillaries using surface binding.

DETAILED DESCRIPTION OF THE INVENTION

In the present invention, it was realized that a capillary segment could be used both to meter reagents and as a reaction container for performing temperature cycling reactions. The length of the capillary and the internal diameter (I.D.) of the bore of the capillary tube define the volume of the interior of the capillary tube segment. Capillaries with a 50–150 um I.D. are commonly available. The small internal diameter of the capillary tubes allows creation of a reaction container having an interior volume less than one microliter. With the present invention, capillaries having volumes from 10–500 nanoliters are adaptable to the preparation of DNA cycle sequencing reactions or any other reaction.

The process carried out by the present automated system is shown in the flow chart of FIG. 2. The process begins by the assembly of the reaction mixture, box 52, by combination of reagents and a sample nucleic acid. The combined reagents are then introduced into the capillaries of a capillary cassette, box 54. The ends of the capillaries are next sealed, box 56. The sealed capillary segments are exposed to thermal cycles, box 58, which effect the cycling reaction. The capillaries of the capillary cassette are then dispensed onto a substrate, box 60. The substrate is then transferred to an analytical system for analysis of the reaction mixture, box 62. Details of this process and the structure of the apparatus for carrying out this process are detailed herein.

In reference to FIG. 1, an automated system is shown for assembly of reaction mixtures, temperature cycling to effect the chemical reaction, and dispensing the volume of the completed reaction mixture onto a substrate for subsequent analysis. In the system an automated robot 102 may move the length of stage 114 and may rotate such that automated robot 102 may be moved in relation to other components of the automated system. The automated robot 102 may be rotated to allow the transfer head 104 on automated robot 102 to access objects on all sides adjacent to stage 114. The assembly of a reaction mixture would begin by the transfer head 104 picking up a capillary cassette from cassette hotel 106.

Capillary cassette 15 is shown in FIG. 3A. The capillary cassette is comprised of a number of capillary tubes 12 extending through a substrate 10. It is preferred that the capillary cassette have at least one row of eight capillary tubes and that the capillary tubes have equal spacing. The capillary cassette shown has substrate 10 with 96 capillary tubes arranged in an 8 by 12 array, with spacing of the tubes matching the spacing of the wells of a 96 well microplate. The length of capillary tubes 12 extending from either side of substrate 10 is unequal. It is preferred that the shorter end of capillary tube segments 12 be shorter than the depth of a microplate well. This allows the short end of capillary tubes 12 to be inserted into the wells of a microplate while substrate 10 rests on the top of the microplate.

The capillary tubes may be made of any material compatible with the assay and preparation to be performed, but preferred capillary materials include, but are not limited to, glass and silica capillaries, although plastic, metals and other materials may also be used. Capillary tubes of various dimensions may be used, such as 75 um ID capillary tubes or 150 um I.D./360 um O.D. capillary tubes.

The capillary tubes 12 extend through a substrate 10 and preferably are arranged in a uniform pattern. The capillary tubes are of equal length and extend through the substrate in a substantially parallel orientation such that each of the two opposing ends of the capillary tubes 12 are coplanar and the planes defined by the ends of the capillary tubes 12 are substantially parallel to the substrate 10. The spacing of the capillary tubes may be uniform and selected to match the center-to-center spacing of wells on a microplate. For example on a standard 96 well microplate the capillary tubes would be arranged with a 9 mm center to center spacing, on a 384 well microplate the capillary tubes 12 would be arranged with a 4.5 mm center to center spacing. Higher density capillary formats, compatible with 1536 well microplates or plates with even higher well density, should also be possible. The capillary tubes 12 are preferably secured within the substrate such that the length of capillary tubes 12 extending from one side of the substrate 10 are shorter than the length of the capillary tube on the opposite side of substrate 10. The length of the capillary tubes 12 on the shorter side of the substrate may be matched to the depth of wells in a microplate, such that the length of the shorter side is a shorter length than the depth of a well in a microplate. This feature enables the capillary cassette to be inserted into a microplate such that the substrate 10 rests against the top lip of the multiwell plate and the capillaries on one side of the substrate may extend into the multiwell plate without touching the bottom. For example, in a 96 well microplate the capillary tubes may be disposed on a substrate such that the shorter side of the capillary tube extending from the substrate may be inserted into wells in a microplate without the capillary touching the bottom of the well. This ensures that liquid dispensed into a well is clear of the capillary to prevent re-entering the capillary.

The capillary cassette substrate 10 may be made of a fiberglass board or other rigid or semi-flexible material. The capillary tubes 12 may be inserted through evenly spaced holes in the substrate and secured with adhesive. In one embodiment, the length and width of the substrate are similar to the length and width of a standard 96 well microplate. This simplifies adapting automated systems designed for manipulation of microplates to handle the capillary cassette.

In some embodiments it may be advantageous to coat the interior of the capillary with various surface coatings such as ionic and non-ionic surfactants. Coatings that may be used include bovine serum albumin (BSA), glycerol, polyvinyl alcohol and Tween 20. The coatings are introduced into the capillary and dried onto the interior surface of the capillary tube. Alternatively, covalent modification of the interior surface with silanization or Griganard reaction may be desired. For example, covalent modification of capillary tubes interior surfaces that reduce electroendoosmosis may also be useful in reducing charge surface effects between a capillary interior surface and components of a reaction mixture. U.S. patent application Ser. No. 09/324,892, hereby expressly incorporated by reference for all purposes herein, discloses the use of acryloyldiethanolamine as a covalent capillary coating with advantageous alkaline stability. In addition to this coating, acrylimide or other known coatings may also be used to covalently modify capillary interior surfaces.

A. Assembly of Reaction Mixture

Returning to FIG. 1, the automated system allows for the combination of reaction reagents and sample DNA using the capillary cassette. A capillary cassette would be taken by transfer head 104 from the cassette hotel 106 and brought into contact with the samples contained in a sample plate at location a. The sample plate is dispensed from sample plate hotel 108. The sample would be drawn into the capillary tubes of the capillary cassette by capillary action. The internal volume of the capillary tube is defined by the length of the capillary tube and its internal diameter. The capillary cassette of FIG. 3A acts as a fixed volume parallel pipettor, allowing a number of capillary tubes to be filled in parallel. Each capillary tube segment will meter a discrete amount of liquid that may be subsequently dispensed.

Once one end of each capillary is inserted into the sample containing well, liquid will be drawn into the capillary. This small amount of sample may be combined with other liquids to form a reaction mixture. The sensitivity of analytical instruments such as a capillary array electrophoresis system and the amplification of reaction mixture products enabled by cycling reactions allow for nanoscale reactions and analysis. Very small-scale reaction are able to reliably produce reaction mixture products of sufficient quantity for analysis on a capillary array electrophoresis system, a capillary electrophoresis chip, a mass spectrometer, or other analysis instrumentation. Significantly less reaction reagents are required if a nanoscale reaction mixture is enabled.

The automated system may be used in various ways to prepare reaction mixtures. A few of the many such methods for use of the system in production of reaction mixtures follow.

Reaction Mixture Preparation Example 1: Metering Reagents with Capillary Cassette and Mixing on a Substrate One method to prepare the reaction mixture is to use the pipettor to separately meter the components of the reaction mixture. For example for a PCR mixture, the nucleic acid sample and PCR reagents would be separately metered and dispensed into a single container in which the liquids are combined. In using the automated system of FIG. 1, the automated robot 102 moves transfer head 104 containing a capillary cassette to location a where a sample plate is located. The ends of the capillary tubes of the capillary cassette are dipped into the wells. The capillary tubes fill by capillary action, metering precise amounts of the samples. The wells of sample plate contain the nucleic acid sample to be PCR amplified. The DNA sample should be sufficiently dilute such that 5–20 ng of DNA is contained in the 10–10,000 nL volume metered by each capillary tube segment in the capillary cassette.

FIG. 4A shows a 16 channel capillary cassette transferring fluid samples from a multiwell plate 36 into a capillary cassette 15. The capillary tube segments 12 on capillary cassette 15 are extended into the wells of multiwell plate 36. The wells of multiwell plate 36 are conical and liquid in the well will flow to the bottom central area of each well. This allows a small amount of liquid within the well to be positioned such that a capillary inserted into the center of the well and above the bottom of the well will contact the liquid. The capillary tube segments of the capillary cassette then fill by capillary action with the liquid in the wells. It is preferred that the capillary cassette have. capillary tube segments which have the same center to center spacing as the wells of the multiwell plate containing the DNA samples. In one embodiment the capillary cassette has the same number of capillary tube segments as the number of wells in a multiwell plate holding samples.

Returning to FIG. 1, after the capillary cassette is dipped into the nucleic acid sample containing wells, the filled capillary cassette may be moved by transfer head 104 to a dispensing device location 122. At the dispensing device location 122, the sample is dispensed onto a substrate. A clean capillary cassette is then retrieved and dipped into a sample plate containing the PCR reagents. As seen earlier, the capillary cassette meters a precise amount of liquid defined by the interior volume of the capillary tubes held in the capillary cassette. The metered amount of reaction reagents may be the same volume as the volume of sample dispensed or it may be different, depending on the requirements of the application. At the dispensing device location 122, the reaction reagents are dispensed from each capillary tube segment onto locations on the mixing substrate containing the nucleic acid sample.

The present reaction mixture assembly may be used for assembly of numerous types of reactions. The same basic method used to assemble the PCR reaction mixture may be adapted to assembly of a cycle sequencing mixture, rolling circle amplification reaction mixture, enzymatic assays, chemical reactions, or other reaction mixtures.

When dispensing the contents into a microplate some care must be taken to mix the sample and reaction reagents in a manner which avoids splattering. A number of different methods have been envisioned to dispense liquid from the capillary cassette.

Capillary Cassette Dispensing Example 1: Centrifugal Force

The first method to dispense the contents of the capillary cassette while avoiding splattering uses a centrifuge to dispense the fluid by centrifugal force. The centrifugal force is applied evenly to all of the capillaries in the capillary cassette such that capillaries independently dispense into the microplate wells. The dispensed liquid is drawn by centrifugal force to the bottom of wells in the multiwell plate.

In FIG. 5A, the centrifuge 42 is shown having a swinging microplate bucket 43 that may contain a multiwell plate with an inserted capillary cassette. The swinging microplate buckets are held on rotor 41.

FIG. 5B shows a cross-section of swinging microplate bucket 43. The capillary tubes 12 of the capillary cassette are inserted into wells 36*a* of multiwell plate 36. The cassette is inserted such that the portions of the capillary tubes 12 extending from the substrate 10 are shorter than the depth of the wells 36a. As shown in FIG. 5B, the capillary tube 12 extending from substrate 10 do not reach the bottom of the wells 36a of multiwell plate 36. Microplate swinging bucket 43 is comprised of an arm 45 and a platform 44. An upper end of arm 45 fits onto latch head 42 on rotor 41. Microplate 36 is positioned on platform 44 of microplate swinging bucket 43. When the centrifuge is in motion, platform 44 rotates on latch head 42 such that the multiwell plate faces the side wall of the centrifuge and the centrifugal force on the liquid in the capillary tubes dispenses the liquid into the bottom of the wells 36a of the multiwell plate 36. When conical shaped wells are used, the centrifugal force will draw the liquids within the well to the well center, causing the sample to locate at a more precise location. The liquid will be displaced from the capillary at fairly low centrifuge speeds.

In FIG. 1, a low speed centrifuge may optionally be included in the automated system at the dispensing device location 122. Automated robot 102 uses transfer head 104 to pick up a microtiter plate dispensed onto location b by microtiter plate hotel 110. Transfer head 104 transfers the microtiter plate to the stage having the low speed centrifuge. A capillary cassette is filled with samples or reaction reagents as described and is transferred onto the microtiter plate on the stage of the low speed centrifuge. The plate and cassette are then spun in the centrifuge, dispensing the liquid from the capillaries into the wells of the microtiter plate. Once the liquid has been dispensed and the centrifuge has stopped rotating, the capillary cassette may by removed by the transfer head and transferred to the cassette washer 118. The transfer head 104 can then pick up a clean capillary cassette from the capillary cassette hotel 106. The clean capillary cassette can be used to meter a second liquid reaction component that is similarly dispensed into the microtiter plate using the centrifuge. In the automated system the centrifuge includes a sensor associated with the rotor used in conjunction with a rotor braking system to stop the rotor in a position that transfer head 104 can access. Such a sensor could be magnetic, optical, mechanical, or use other known means of sensing rotor position.

Capillary Cassette Dispensing Example 2: Air Displacement

A second method of dispensing the liquid contained in the capillary tube segments of a capillary cassette is through the use of an air displacement device. With reference to FIG. 1, a microtiter plate dispensed from microtiter plate hotel is transferred by transfer head 104 to the dispensing device location 122. At this location an air dispenser, such as the one pictured in FIG. 4A–C is located. Subsequently a capillary cassette is retrieved by transfer head 104, and filled with either sample from a sample multiwell plate or with reaction reagents. The capillary cassette is then moved to the dispensing device location 122 and brought into contact with air displacement head. The substrate of the capillary cassette is placed on a receiving platform on the air displacement head. Alternatively, the air displacement head may be joinable to automated transfer robot 102.

With reference to FIG. 4A, the air displacement head 301 is shown with a capillary cassette 15 held on bottom plate 302. The bottom plate 302 is attached to a manifold assembly by hinge 318. Capillary cassette substrate 10 is held on foam rubber pad 304 that is secured onto bottom plate 302. An array of holes 325 extend through foam rubber pad 304 and bottom plate 302, which are spaced to allow the capillary tubes 12 to extend through foam rubber pad 304 and bottom plate 302 when the capillary cassette is positioned on bottom plate 302. The manifold assembly of the air displacement head is comprised of an upper housing 306, chamber unit 310 and a set of clamps 314. Clamps 314 secure membrane 312 to the lower surface of the chamber unit 310. Membrane 312 forms a seal to the top surface of the capillary cassette 15 when the manifold assembly is closed over the cassette. Membrane 312 has holes 316 corresponding to capillary positions in the cassette when the capillary cassette 15 is placed on bottom plate 302. When the top manifold of air displacement head 301 is closed against bottom plate 302, capillary tubes 12 are positioned extending through capillary tube receiving holes 316 on membrane 312. When the air displacement head 301 is closed it may be secured by latch 322 which mates with hole 324 to clamp the capillary cassette between the foam rubber pad 304 and membrane 312 resulting in a seal between the top surface of cassette 15 and the membrane 312.

FIG. 4B illustrates a cross sectional view of displacement head 301. Upper housing 306 is constructed of metal, acrylic or other rigid material. Gas input coupler 303 is disposed on upper housing 306. When a pressurized gas or vacuum line 305 is attached to gas input coupler 303, a vacuum or pressure force may be introduced into upper chamber 307. Held between upper housing 306 and chamber unit 310 is a gas impervious elastic membrane 308. The area between elastic membrane 308 and upper housing 306 defines upper chamber 307. Secured onto clamps 314 is membrane 312. Membrane 312 is pressed against substrate 10 of a capillary cassette inserted into displacement head 301. Substrate 10 is secured within displacement head 301 by bottom plate 302. Rubber pad 304 provides a deformable surface that exerts uniform force pressing substrate 10 against membrane 312. Membrane 312 has an array of holes 316 that allow the capillaries 12 of the capillary cassette to extend through membrane 312. When a capillary cassette is inserted into air displacement head 301, the substrate seals holes 316 enclosing lower chamber 313. When pressurized gas is introduced into chamber 307 by gas line 305, elastic membrane 308 will be pressed into lower chamber 313. Membrane 308 is located between upper chamber 307 and lower chambers 313. Membrane 308 serves both as seal for the upper end of chambers 313 and the chamber displacement actuator when pressure is applied to the upper chamber 307 through coupler 303. The degree of displacement is dependent on the pressure applied and the elasticity of membrane 308. The resulting air displacement will act to dispense liquid from capillary tubes 12 that extend through the capillary cassette 10 and into the lower chamber 313. By regulating the amount of pressure applied through line 305, a consistent displacement force will be applied to each capillary tube. Given the submicroliter volume of the capillary tube segments, fluctuations in the amount of dispensing pressure should not adversely affect displacement from the tubes.

FIG. 4C illustrates the closed air displacement head 301. Upper housing 306 is pulled toward bottom plate 302 by latch 322 in order to compress membrane 312 against the top of the capillary cassette substrate thereby forming a seal. Clamps 314 secure membrane 312 onto chamber unit 310. Air displacement head 301 is mounted on arm 320. Arm 320 may extend from automated transfer robot 102 shown in FIG. 1 or be positioned at dispense location 122. Pressurized gas may be introduced into upper housing 306 through gas input couple 303.

This displacement head provides an individual displacement chamber for each of the capillaries dispensed. Although a 16 capillary cassette is depicted, the displacement head may be constructed to dispense capillary cassettes having an array of 96 capillaries or greater capillary densities. The dispensing force applied to each capillary is sufficiently small to allow dispensing directly onto a substrate with the sample dispensed at a discrete location.

Air displacement or centrifugal displacement may be used to dispense liquid from the capillary tube segments in a capillary cassette. It may also be possible to dispense liquid from the capillary tubes using a bank of syringe pumps, applying pressure through a gas permeable/liquid impermeable (hydrophobic) membrane, using electrokinetic dispensing, or other known dispensing means. The air displacement head may also be used to dispense finished reaction mixtures onto a substrate for subsequent analysis.

Reaction Mixture Assembly Example 2: Dehydrated Reagents

A second method to assemble the reaction mixture is to have the regents required for the reaction stored as a dehydrated coating either on the interior of a capillary or on a substrate, such as within a well of a multiwell plate. If the reaction reagents were dehydrated onto the interior of capillary tube segments in a capillary cassette, introducing a sample into the capillary would cause rehydration, mixing and formation of the reaction mixture. In a similar manner, if the wells of a microplate were coated with the dehydrated reaction reagents, adding a nucleic acid sample into the wells would bring the reaction reagents into solution, forming an assay mixture. The sample could be metered with a capillary cassette and dispensed from the capillary cassette by one of the methods set out above. The sample would bring the dehydrated reaction reagents into solution and mix with the sample containing nucleic acid by diffusion. This provides a method to assemble the reaction mixture in a very simple manner, potentially without the need to dispense the capillary tubes with a centrifuge or air displacement device. This could both simplify the reaction processing system and shorten the reaction assembly time.

For PCR, a dehydrated reagent mixture is commercially available, sold as Ready-to-Go® (Amersham Pharmacia Biotechnology, Piscataway, N.J.). The stabilized, dehydrated reagents may be coated onto the interior surface of capillary segments or the interior of the wells of a multiwell plate. The Ready-to-Go® product uses a carbohydrate matrix to stabilize the reaction reagents (DNA polymerase, buffer reagents, dNTPs) in a desiccated state. Bringing the reagents in the Ready-to-Go® mixture into solution with the liquid nucleic acid sample and primers in solution produces the final reaction mixture required for the reaction. The combination of the stabilized Ready-to-Go® compounds, the template DNA, primers, and sufficient water produces a final reaction mixture. It is contemplated that reagents for chain termination sequencing reactions and other reactions could also be stored in a desiccated state.

The coating could be applied to surfaces by a number of different methods including vapor phase coating, filling a capillary (by capillary action, pressure filling, etc.) with the Ready-to-Go® mixture and emptying the bulk phase (under vacuum, pressure or other forces), or dipping a substrate (such as a bead) into the reagents and subsequently drying the bead.

Reaction Mixture Assembly Example 3: Solid Phase Capture

A third method of assembly of the reaction mixture is to capture material from the sample on the surface of a substrate, such as the interior of a capillary tube segment. The material captured can be nucleic acid, enzymes, other biopolymers, or chemicals. The desired material from the sample may be attached onto the surface by a number of methods. These include covalent attachment, binding by antibodies, DNA hybridization, hydrophobic interactions, electric field, magnetic field, or other chemical or physical forces. Once the sample has been attached, the remaining liquid in which the sample was suspended may evacuated from the capillary or microchip by chemical reaction or physical force. Air displacement or centrifugal dispensing method may be used to empty the capillary, as can a vacuum. The sample material would remain on the surface of the substrate. In this single step, the sample material may be substantially purified. The reaction reagents may then be combined with the sample material, producing the reaction mixture.

For nucleic acids, one method to immobilize a nucleic acid sample is to attach the nucleic acid directly to a surface. This may be done by non-covalent modification (such as surface treatment with NaSCN, DMSO, etc.) or covalent linkage. There are a number of different covalent attachment methods for DNA known in the art. For example, an amino group can be attached to the deoxyribose base of DNA and incorporated during a synthetic reaction, such as during PCR amplification of a DNA plasmid insert. The glass or silica of a capillary interior could be silanized and the amino group on the modified DNA would covalently bond to the silanized interior of the capillary. Alternatively, other chemistries are available to covalently immobilize DNA onto a surface. Once the DNA is bound to the surface of a capillary or other substrate, the liquid in which the DNA was suspended may be eliminated from the capillary and the capillary may be filled with reaction reagents.

An alternative method of attaching a nucleic acid to the interior of the capillaries of a capillary cassette is through affinity chemistry. One common affinity chemistry procedure labels a biomolecule with biotin and then binds the biotinylated biomolecules to avidin or streptavidin. The avidin/streptavidin may be used to link the biotinylated molecules. Nucleic acid labeled with biotin may be subsequently attached to a surface, such as the interior of a capillary tube. This may be accomplished by binding streptavidin to the interior of the capillary.

One example of the use of affinity chemistry for the binding of DNA to the interior of a capillary is disclosed in U.S. Pat. No. 5,846,727, hereby expressly incorporated herein for all purposes. This reference describes the binding of DNA to the interior surface of the capillary tubes. The technique requires primers labeled with biotin that are combined with dNTPs, a DNA polymerase, and a reaction buffer. This is combined with template DNA, such as plasmids or M13 from a DNA library with sub-cloned DNA inserts, to form the reaction mixture. In the present invention a microplate may contain 96 or more reaction mixtures, each with a unique template with a subcloned DNA sequence. This reaction mixture could be assembled by the method stated in reaction mixture assembly example 1: namely the reaction reagents and the template sample could be separately metered and dispensed into a 384 well microtiter plate. In a microplate well the liquids are combined to form a reaction mixture. The reaction mixture is metered into the capillary tube segments of a capillary cassette. The PCR reaction may be effected by temporarily sealing the ends of the capillary tube segments and exposing the capillary cassette to thermal cycles, as described below. The results of the PCR reaction are exponentially amplified copies of the subcloned plasmid DNA insert containing the biotin labeled primer.

The PCR amplified DNA containing the biotin labeled primer may then be immobilized on the walls of the capillary tubes of a capillary cassette. The immobilization capillary cassette would have capillary tubes with avidin or streptavidin coated onto the interior surface of each capillary tube. The chemistry for attachment of avidin/streptavidin may be that disclosed in, for example, L. Amankwa et al., "On-Line Peptide Mapping by Capillary Zone Electrophoresis," Anal. Chem., vol. 65, pp. 2693–2697 (1993). The capillary is filled with (3-aniopropyl)trimethoxysilane (3-ATPS), incubated for 30 minutes, and air dried. The dried capillaries in the capillary cassette are next filled with sulfosuccinimidyl-6-(biotinamido)hexonate (NHS-LC biotin) which is again incubated followed by air drying. Avidin or streptavidin in phosphate buffer at 7.4 pH is added to each capillary tube. The avidin binds to the biotin immobilized on the interior of each capillary. The double stranded amplified biotinylated PCR products suspended in a buffer (e.g. Tris-HCl, or EDTA with either NaCl or LiCl at 1–3M added for efficaceous binding) are added to the capillary tube and incubated for 5–10 min. This results in a capillary wall modified as follows: capillary wall—Si—$C_3H_6$—NH—CO-biotin-avidin or streptavidin-amplified oligonucleotide with associated biotin primer.

In this embodiment biotin, rather than avidin or streptavidin, is covalently attached first to the capillary wall. This aids in the regeneration of the capillary cassette for subsequent binding reactions. After completing the cycle sequencing reaction, it would be difficult to remove the amplified biotinylated DNA without also denaturing the avidin protein. By having biotin bound to the interior surface of the capillary the amplified DNA may be easily removed by filling the capillary with phenol or formamide solution at 65–90 degrees C. This denatures the avidin protein without removal of the biotin bound to the interior surface of the capillary. This mixture is then dispensed. The capillary cassette may then again be filled with the avidin containing solution and reused for binding subsequent biotinylated amplified template DNA.

Once the DNA is immobilized on the interior surface of the capillary, the contents of the capillary tube may be dispensed in one of the methods described and the DNA would remain bound to the surface of the capillary. This removes debris and other impurities from the DNA presenting a rapid and effective method of DNA purification. The capillary may be rinsed with a buffer for additional purification. The defined area of the interior surface of the capillary provides a known amount of binding sites for the DNA attachment. This provides a simple method for normalization of DNA concentrations. The normalization of DNA concentrations is important in improving the success rate of CAE analysis of cycle sequencing reactions. The capillary cassette may then be dipped into wells or a reagent reservoir containing the reagents for cycle sequencing. The cycle sequencing reaction can be performed by temporarily sealing the ends of the capillary tubes by pressing each end of the capillary tubes against a deformable membrane. The capillary cassette may then be exposed to thermal cycles that effect the cycle sequencing reaction.

Prior to filling, the capillary tube segments of the capillary cassette may be coated with a variety of compounds. Coating the interior surface of the capillary tube segments with bovine serum albumin (BSA) or polyvinyl alcohol has been shown to improve performance of some reactions, such as preparation of chain termination sequencing reactions.

B. Thermal Cycling

Once the reaction mixture is introduced into the capillary tube segments of the capillary cassette, the ends of the capillaries of the capillary cassette are sealed and the capillary cassette is exposed to temperature cycles. The ends of the capillary cassette capillaries are sealed by pressing each of the ends of the capillary tubes against a deformable membrane. Returning to FIG. 1, once the capillary cassette has been filled with the reaction mixture, the ends of the capillaries are sealed and the capillaries are exposed to thermal cycles in thermal cycling device 116.

In one thermal cycling device, shown in FIGS. 7A–7C, the thermal cycling device has integrated membranes that seal the ends of the capillaries and exposes the capillary cassette to thermal cycles. In this apparatus the means for sealing the ends of the capillaries in the capillary cassette is incorporated into the thermal cycling device.

With reference to FIG. 7A and 7B, the capillary cassette 15 is held on lip 280 within internal passageway 256 between deformable membranes 264a and 264b. As seen in FIG. 7B, deformable membrane 264a is mounted on upper platform 261. Lid 262 is secured on upper platform 261. Platform 261 is attached by pivot 286 to base 265. Pneumatics 284a, 284b are attached at an upper end to upper platform 261 at pivot 263. Screw 282 acts as a stop for upper platform 261 when upper platform 261 is lowered onto housing 270, enclosing internal passageway 256. Diffuser 258 promotes temperature uniformly of air circulating in internal passageway 256. Thermocouple 260 measures temperature of the circulating air. The function of pivot 277 and bottom membrane platform 200 is described in conjunction with FIG. 7C.

FIG. 7C shows a cross section of the capillary cassette holding chamber with capillary cassette 15 inserted into the internal passageway 256. The capillary cassette could be inserted into this area by automated robot 102 of FIG. 1 after the capillary tube segments have been filled with the samples and reaction mixture.

Capillary cassette 15 is positioned such that substrate 10 rests on ledge 280. Capillary cassette is positioned such that the ends of capillary tube segments 12 are depressed against top deformable membrane 264a and bottom deformable membrane 264b when upper platform 261 is lowered over the capillary cassette and lower platform 271 is raised. Lid 262 seals against housing 270 when upper platform 261 is lowered to provide a flush seal. Screw 282 acts as a stop for upper platform 261 to prevent the platform from lowering so far that capillary tube segments are bowed or damaged. Base platform 266 is secured to post 273 and secured to housing 270. The lower end of pneumatics, 284b is secured at a lower pivot 271a to lower platform 271. Extending through lower platform 271 are shoulder screws 268 which extend through housing 270 and stationary platform 266 and are secured to lower platform 200. When upper platform 261 is lowered by pneumatic 284b lower platform 271 is also raised toward housing 270. When pneumatic cylinders 284b, 284a are retracted, the pneumatic cylinders move to a vertical orientation. Upper platform 261 is lowered and lower platform 271 is raised slightly in an arc. Lower platform 271 will arc upward on pivot 277 to move to a position substantially parallel to upper platform 261 when pneumatic cylinder 284b is fully retracted. When a capillary cassette 15 is inserted into internal chamber 258 the ability of platform 200 to "float" on springs 275 prevents excess pressure from damaging capillary tubes 12 or membranes 264a, 264b. Platforms 261 and 200 exert 400 pounds per square inch force on capillary tubes 12 providing sufficient sealing pressure. With upper platform 261 lowered, the capillary tube segments 12 are sealed at each end by deformable membranes 264a, 264b. Deformable membranes 264a, 264b may be made of silicon rubber or other deformable material.

Returning to FIG. 7A, a motor 250 turns shaft 251 that rotates squirrel cage blower 253. Blower 253 produces air movement through diffuser 254 to flow into internal passageway 256. The blower generates sufficient circulation flow that the air flowing through internal passageway 256 circulates at 2,000 feet per minute. Diffuser 254 ensures that the heat of the air blown by blower 253 is uniform throughout passageway 256. Cone 255 on diffuser 254 aids in mixing the flowing air, promoting temperature uniformity through passageway 256. Diffuser 254 acts to ensure an even flow of air through passageway 256 in the region of the capillary cassette and reduces non-uniformity from wall loss effects in internal passageway 256.

The internal passageway 256 is defined by outer housing 270. Outer housing 270 is preferably of rectangular cross section and comprised of sheet metal, plastic or other durable materials. The internal surface of outer housing 270 at all locations except for inlet 278 is lined with thermal foam insulation 272. Insulation 272 prevents excess heating of outer housing 270 and helps retain heat and aids temperature uniformity of the air circulating through internal passageway 256. After flowing through first diffuser 254 the air flows through second diffuser 258. Diffusers 254 and 258 promote uniform air flow and temperature uniformity through internal passageway 256. Past first diffuser 254 internal passageway 256 transitions to match the dimensions of the capillary cassette. The heated air flows past thermocouple 260 that is vertically disposed at the center of internal passageway 256 just beyond second diffuser 258. Thermocouple 260 acts to monitor the temperature within internal passageway 256. Thermocouple 260 may be a temperature-monitoring device inserted into a capillary tube section that extends through outer housing 270 and through foam insulation 272. Alternatively thermocouple 260 may be selected such that it accurately reflects the internal temperature of a capillary tube.

The air circulating through internal passageway 256 passes thermocouple 260 and flows past the capillary tube segments 12 of capillary cassette 15. The ends of the capillary tube segments are sealed at their upper end by deformable membrane 264a mounted on upper platform 261 that has been lowered to form an air tight seal with housing 270. The lower ends of capillary tube segments 12 are sealed by deformable membrane 264b. Deformable membrane 264b is mounted on platform 200 that is secured on a bottom surface by shoulder screws 268. Shoulder screws 268 extend through housing 270 and retained by platform 271. Springs 275 located between platform 200 and platform 271 provide a biasing force while allowing for platform 200 to float such that the deformable membrane 264b is biased against the ends of capillaries 12. The function of double acting pneumatics in sealing lid 262 and applying force to position platform 271 is described in conjunction with FIG. 7C. Lid 262 fits onto housing 270 such that the sheet metal or other material comprising the edge of lid 262 fits on top of housing 270. Membrane 264a is mounted on upper platform 261 preferably such that membrane 264a extends into internal passageway 256 at least far enough that membrane 264a is even with insulation 272. As the air travels past capillary tube.segments 12, the length of the capillary tube segments 12 below substrate 10 are rapidly heated and cooled to the temperature of the air rapidly moving through internal passageway 256.

Door 274 controlled by motor 276 is used in conjunction with thermocouple 260 and heating element 252 to control the temperature within internal passageway 256. When door 274 is closed, the air circulating within internal passageway will not be exchanged with outside air. As the air continuously passes over heating element 252 the air is rapidly heated until the air comes to the selected temperature. Once thermocouple 260 senses that the temperature is at a selected temperature, heating element 252 may be kept at a lower heat output such that the internal temperature is maintained. If the temperature needs to be rapidly dropped, as in during a thermal cycling reaction, door 274 may be moved to orientation 274a by motor 276 with the door 274 moved into internal passageway 256, allowing all air which has passed capillary cassette 15 to be exhausted from internal passageway 256 to the outside. It is envisioned that a filter or exhaust duct could be mounted about door 274 to prevent compounds in the circulating air from being exhausted to the environment. The rapidly circulating air will be quickly exhausted to outside of the thermal cycler while ambient air is drawn in through air intake 278. Air drawn into internal passageway 256 through intake 278 flows through heater 252. The area through which the air moves is restricted by block 259 positioned above heater 252 within internal chamber 256. Again the temperature of the air within internal passageway 256 is monitored by thermocouple 260 and when the desired temperature drop has occurred, door 274 will be brought toward housing 270, reducing air volume drawn through air intake 278.

By connecting heating element 252, thermocouple 260 and door motor 276 to an electronic control system, such as a computer controller, this thermal cycler may perform precise air temperature varying sequences. Additional heat is added when needed by heating element 252 and heat is exhausted by opening door 274, with the temperature result of either action monitored by thermocouple 260. Exhausting circulating air through door 274 allows air within internal passageway to drop in temperature at a rate greater than 10 degrees per second.

The rapid temperature change combined with the rapid transfer of heat to or from the capillaries allows for efficient temperature cycling reactions. For example in reactions using a thermostable polymerase, the denaturing of nucleic acid strands and the annealing of primer to template strands each may take place in one to five seconds. The extension of the primer will require less time to effect since the rapidly circulating air and the thin walls of the capillaries rapidly bring the internal volume of the capillaries to the selected temperature. The thin walls of the capillaries and the small capillary volume enable a rapid temperature change and heat transfer throughout the internal capillary volume. This greatly reduces the time required for each cycle of the reaction, allowing more efficient use of the thermal cycler and greater throughput in sample preparation. Presently, a 30 cycle PCR amplification may be performed in under 30 minutes. It should be possible to reduce this time to less than 8 minutes.

Once the thermal cycling reaction is complete, upper platform 261 may be raised and capillary cassette 15 removed from internal passageway 256. During the temperature cycling process, the liquid within each capillary tube segment will expand somewhat and some liquid will leak from the capillary and be carried away by the rapidly flowing air. However, such loss is only a few percent of the volume of the capillary tube segment and should not present either a contamination problem or cause enough reaction product loss to materially affect subsequent analysis. To prevent the small opening of capillaries 12 from being contaminated by the small residual of material on deformable membranes 264a and 264b, if desired, disposable materials such as a thin film can be placed over the deformable membranes. The disposable materials can be individual sheets or rolls of material that advance after each use to prevent the capillary openings from touching a section of material previously used. In addition, the portion of capillary tube segments 12 located between substrate 10 and deformable membrane 264a will receive only poor air flow and will be less likely to rapidly reach the denaturation temperature. However since this length is short, the failure of this area to as rapidly reach the denaturation temperature should not adversely affect the ability of the remaining portion of the capillary from producing sufficient reaction product for subsequent analysis.

An alternative device for sealing the ends of the capillary is a capillary cassette holder that seals the ends of capillary tube segments of a capillary cassette. With reference to FIG. 3B the capillary cassette holder is comprised of a pair of parallel deformable membranes 14a, 14b each secured onto platforms 16a, 16b. The deformable membranes may be silicon rubber seals, Teflon®, plastics or other resilient, deformable material. A pair of parallel posts 9 extend from bottom platform 16a to top support platform 24 where the posts are secured by internally threaded nut 18. Post 9 passes through platform 24 and nut 18 is retained on an annular lip of platform 24. Shoulder screws 20 extend through holes in support 24 and are secured to top platform 16b. Springs 22 bias the top platform 16b against the ends of capillary tube segments 12 while allowing 16b to float. The substrate 10 of capillary cassette 15 may be designed to have holes which conform to the spacing and dimension of posts 18 such that capillary cassette 15 may be more easily and securely held within holder 23.

Once the ends of the capillary cassette are sealed in holder 23, the combined capillary cassette and holder may be exposed to thermal cycles. The holder seals 16 capillaries. However, a holder may be designed to hold capillary cassettes having 96 capillaries or higher densities of capillaries. In addition to capillary cassettes, chips of other substrates may be used as the reaction containers. FIG. 3E shows a chip substrate 70 comprised of two bonded substrate layers 72, 74. One layer 72 has grooves 76 extending the length of the chip. The affixed top substrate 72 encloses a capillary dimension passage 76 with opposite open ends. A liquid reaction mixture may be introduced into the enclosed passage. The ends of these passages may be sealed by pressing the ends against a deformable membrane, as was done with the capillary cassettes. Temperature cycling may require longer times because of greater mass material comprising the chip, but cycling times should still be more rapid than conventional cycling.

For isothermal reactions, such as rolling cycle amplification, temperature cycling is not required to effect the reaction. Once an isothermal reaction mixture is combined and introduced into a capillary cassette, incubation of the cassette at a reaction temperature will allow the reaction to occur. With reference to FIG. 1, the automated transfer device may transfer a capillary cassette into incubator 124 where the capillary cassette is incubated at a selected temperature. A set of deformable membranes may be used to seal the ends of the capillaries during incubation. As was seen in other system components, incubator 124 may be used at the same time as other system components.

In the case of PCR or chain termination sequencing reactions it is necessary to expose the reaction mixture to temperature cycles. In FIG. 1 the transfer head 104 moves the capillary cassette into thermocycler 116. The thermocycling device may be any device that can expose the capillary tube segments of the capillary cassette to temperature cycles. Thermal cycling devices that use water, electric field, heating blocks, or other means may be used. Alternatively, air based thermal cycling devices are rapid and adaptable to the low volume cycling of the present invention.

A thermal cycling device that uses air as the temperature transfer medium is shown in FIG. 6. The reaction mixture is contained in capillary tube segments that have a high surface to volume ratio and small material thickness. This allows very rapid transfer of heat through the walls of the capillary and throughout the liquid reaction mixture. An equilibrium temperature is reached rapidly throughout the liquid in the capillary. The use of air as a heat transfer medium enables the rapid ramping of temperature in the reaction chamber. Rapid circulation of the air ensures rapid and more uniform heating or cooling of the capillary segments and their contents.

With reference to FIG. 6, the capillary cassette 15 sealed within holder 8 is inserted through opening 215 in housing 202 of the air based thermal cycler. The holder 8 is supported by housing surface 215 of the thermal cycling chamber 210. The capillary tubes 12 mounted to substrate 10 are exposed to the air of thermal cycling chamber 210 such that the air may freely flow around capillary tube segments 12. Thermocouple 216 monitors the temperature of the air moving past capillary tubes 12.

In the air based thermal cycling device, paddle 208 driven by motor 206 rapidly circulates air within chamber 210. The air is rapidly circulated past the capillaries 12 of capillary cassette 15. Halogen bulb 220 acts as a heat source to heat the air within the thermal cycling chamber 210. To effect a thermal cycling reaction, the circulating air is held at a selected temperature for a selected period of time. The thermocouple 216 transmits the temperature of the capillary tube segment 12 to microprocessor 218. To effect the needed temperature changes the microprocessor instructs actuator 222 to open door 226 allowing air to pass through vent 224. As air passes through vent 224 additional air is drawn into the reaction chamber through air inlet 203 by fan blade 204. Fan blade 204 is driven by motor 206. The venting of hot air and replacement with cooler ambient temperature air, combined with the rapid circulation of air by fan 208, a relatively small thermal cycling chamber 210 and precise measurement of sample temperatures by thermocouple 216 enables rapid temperature ramping. The time required for effecting the thermal cycles is greatly reduced. A typical thermal cycling reaction requires different temperatures for denaturing of nucleic acid strands, annealing of a primer, and extension of a polymerase. The denaturing and annealing steps occur rapidly in a capillary tube where the small internal volume of liquid will rapidly come to equilibrium, while the extension of the DNA molecule takes less than 10 seconds for a 500 base extension. The time required for each thermal cycle of the three temperatures (annealing, extension, denaturing) may be reduced to less than 15 seconds by using the rapid heat transfer of the air based thermal cycling apparatus. A program of 30 cycles, each cycle exposing the capillary to three temperatures for varying amounts of time, theoretically may be effected in less than 8 minutes.

The use of the capillary cassette in combination with an air based thermal cycler allows additional advantages. The capillary cassette holder temporarily seals the capillary, allowing rapid and simplified sealing of each capillary tube segment. The capillary cassette contains a number of capillary tubes in parallel arrangement, allowing for more efficient use of the thermal cycler and allowing greater sample throughput. Once the thermal cycles are completed the capillary cassette 15 contained within holder 8 is removed through opening 215. The capillary cassette 15 is released from the holder and is subsequently dispensed.

The thermal cyclers of FIGS. 6 and 7A–C were illustrated as being used with capillary cassettes. The same devices are adaptable to other containers with opposing ends. For example, a chip-like substrate with a plurality of passageways extending through the chip (as seen in FIG. 3E) has, like a capillary cassette, evenly spaced opposed open ends. Several chips could be placed into a thermal cycler with the open ends temporarily sealed and exposed to thermal cycles. The rapid temperature changes may be a bit slower due to increased material thickness. Other containers with opposing open ends may also be used with either temperature cycling device.

C. Dispensing Completed Reaction Mixture

Following the completion of the thermal cycling or isothermal reactions, the prepared reaction mixture is dispensed into a substrate for analysis by an analytical system. As noted above, the capillary cassette may be dispensed by air displacement, centrifugal force, vacuum or any other displacement method. The substrate into which the reaction mixture is displaced may be the wells of a multiwell plate, locations on a planar substrate, or wells that lead into an analytical chip. The reaction mixture, though small, still may produce enough reaction products that dilution is necessary.

Dispensing Completed Reaction Mixture Example 1: Direct Dilution

In reference to FIG. 1, following completion of the temperature cycling process, the capillary cassette may be removed from air thermal cycler 116 by transfer head 104. The capillary cassette may be moved by transfer head 104 to be placed in a plate dispensed from finished sample hotel 112. The plate, located at position c, may be a multiwell plate such as a 384 well microplate. The wells of the plate contain a dilution liquid, such as formamide, water, TBE, or other selected buffers. The reaction mixture may be dispensed from the capillary tube segments of the capillary cassette by positive displacement, centrifugation, or other dispensing means. The reaction may also be dispensed into a solution for further chemical or biochemical reaction.

Dispensing Completed Reaction Mixture Example 2: Ethanol Precipitation

Ethanol precipitation may be effected in a dispensing means similar to the means of direct dilution. Transfer head 104 of FIG. 1 would again take the capillary cassette from air thermal cycler 116 and place the short ends of the capillaries in a multiwell plate located at position c. In this case the wells of the plate would contain an alcohol, such as 90% ethanol chilled to 4° C. The reaction mixture would be dispensed from the capillary cassette into the ethanol by centrifuge. Air displacement or other dispensing methods can also be used. After allowing time for the precipitation, the multiwell plate can be moved into the centrifuge by transfer head 102 and a low speed centrifugation performed to collect the precipitated nucleic acid in the bottom of the multiwell plate. The alcohol could then be removed by aspiration or other means. The precipitated DNA could then be resuspended in formamide, water or other suitable diluent. Once the sample plate is prepared, by either direct dilution or ethanol precipitation, the plate may be transferred by transfer head 104 to analytical stage 120. Analytical stage 120 may feed the sample plate directly into an analytical device, for example a capillary array electrophoresis system, such as MegaBACE™ produced by Molecular Dynamics, Sunnyvale Calif. Alternatively, the analytical stage could direct the product to other systems for further processing. It is also possible to dispense the samples onto a substrate for mass spectrometry analysis, calorimetric analysis, or other analytical methods.

Dispensing Completed Reaction Mixture Example 3: Dispense Directly into Analytical System In the previous two examples the samples were dispensed into multiwell plates. These plates could then be moved manually or robotically onto a stage for analysis by an analytical system. Alternatively the capillary cassette could be dispensed directly into the wells of an analytical device, such as an electrophoresis chip. For example a capillary cassette having 16 capillaries disposed in the substrate in two parallel rows of eight capillaries may dock with 16 wells in an analytical microchip. Such a microchip would have an array of analytical lanes in fluid communication with a sample port.

The capillary cassette may be designed such that the spacing of the capillaries matches the spacing of the sample reservoir inlets. For example, the capillary cassette illustrated in FIG. 3C includes capillaries 12 extending through flexible strip 11. Flexible strip 11 may be used alone or in combination with other such strips. The orientation of the capillaries in an essentially straight line may be altered by bending strip 11 to form an arc. FIG. 3D illustrates strip 11 bent to allow capillaries 12 to mate with input ports that are disposed on a substrate in a circular pattern. The liquid in capillaries 12 may then be electrokinetically injected or otherwise dispensed from capillaries 12 into ports of an analytical chip if an appropriate electrode array or other dispensing methods are used. Strip 11 may be positioned in the curved orientation by pressing strip 11 against a curved form, such as a curved metal block. This may be done by an automated strip mover incorporated into an automated sample preparation system. The capillary cassette could be dispensed by air displacement or other dispensing means preferably selected to minimize splattering and bubble formation. Prior to dispensing the prepared reaction mixture into the wells for analysis, a small amount of a dilutant could be added to each analytical microchip well. When the capillary cassette is dispensed, the diluent will dilute the samples in the sample wells. The sub-microliter volume reaction mixtures prepared in the capillary cassette, such as a DNA sequencing reaction product mixture, can readily be integrated with the analytical microchip for sequencing or other analysis methods.

D. Washing Capillary Cassettes

Following each use of a capillary cassette, the capillary cassette may be disposed of or it may be washed and reused. After the contents of the capillary cassette have been dispensed or a capillary cassette has otherwise been used, the capillary cassette is taken to cassette washer 118 where the cassette is washed. Following washing, the cassette is returned to the cassette hotel 106 where the cassette may be reused.

With reference to FIG. 8A, capillary cassette washer 410 is comprised of wash manifold 412 and wash tank stage 416. Between wash manifold 412 and wash tank stage 416 is capillary cassette platform 414. Extending from wash tank stage 416 is leg 419. In this wash system, a wash liquid is pumped from one or more of containers 452, 454, 456, 458 through respective tubes 1, 2, 3, 4 into respective router inputs 453, 455, 457, 459. The router directs the selected wash fluid through router outflow 451 through line 451a into the wash tank 440. The fluid is drawn from wash tank 440 through capillary tube segments of a capillary cassette. The capillary cassette substrate is held between wash manifold 412 and wash tank 440 such that if suction is applied to wash manifold 412, wash fluid will be drawn through capillary tube segments from wash tank 440. The wash solution is drawn by vacuum through wash manifold 412 and into waste receptacle 490.

FIG. 8E provides a schematic of the working of the wash station. Nitrogen tank 460 provides a pressure source to direct fluid flow. Opening manual valve 462 allows gas to flow through regulator 466 and through filter 468. Regulator 466 regulates the pressure from the pressure source. Pressure sensor 464 monitors gas pressure from the nitrogen source and indicates if gas pressure is below a selected pressure. The pressurized gas flows through filter 468 into line 470. Pressurized gas line 470 branches into the top of sealed wash bottles 471, 472, 473, and 474. The pressurized nitrogen pumps the wash liquid within each wash bottle into respective fluid lines 471a, 472a, 473a and 474a respectively through an intake filter 476 on each of said respective fluid lines. Each of the sealed wash solution bottles may contain a different wash solution, such as water, alcohol, a buffer or other wash solution. Although four wash bottles are illustrated, the system is adaptable for use with more or fewer wash fluids. In addition, exchange of wash bottles simply requires venting nitrogen pressure on bottles 471, 472, 473, 474 at valve 462, the removal of the cap from the selected bottle and replacement of the cap with attached pressure and fluid lines into a new or refilled wash fluid bottle. Each of the fluid lines 471a, 472a, 473a and 474a terminate in selector valve 478. According to a preset program, the selector valve routes one of the selected fluids from the input line into valve output line 480. The valve output line then transports the pressurized liquid into wash tank 440.

The capillary tubes in the capillary cassette function as a conduit for transport of fluid from the wash tank 440 into the wash manifold interior 425. Vacuum source 496 provides a vacuum force once valve 492 is open. When vacuum valve 498 is open, a vacuum force is directed into waste bottle 490 creating negative pressure within line 490a. When valve 495 is open, suction will be applied through suction line 490a, suction line 495a and suction lines 424a. As suction is applied through suction ports 424 by suction lines 424a the negative pressure through interior wash manifold 425 will draw liquid up through the capillary tube segments extending into wash manifold interior 425. The liquid will travel through suction passageways 424, into suction lines 424a, past valve 495, through suction lines 495a and 490a and into waste bottle 490.

FIG. 8D illustrates a view of the wash manifold. The bottom of the wash manifold contains holes 426 into which the capillaries are inserted. Wash manifold interior 425 is comprised of lanes joined at a first end to suction passageways 424 and at a second end to purge passageways 423. When suction is applied through line 424a fluid will be drawn through capillaries into the lanes comprising interior 425, through passageways 424 and into line 424a. When the purge valve is opened, air will pass through line 423a, through passageway 423, into interior 425, and into passageway 424, clearing interior 425 of any liquid remaining in interior 425.

Following a wash procedure, wash tank 440 is lowered relative to the capillary cassette platform such that the ends of the capillary tube segments are not in contact with the liquid in wash tank 440. The liquid within wash tank 440 is drained through drain 484 which transmits the fluid into drain line 484a when valve 485 is opened and suction is applied through suction line 490a. The fluid within wash tank 440 will then drain into waste bottle 490.

Before each wash solution is introduced into wash tank 440, wash fluid supply line 480 and the wash tank distribution manifold 480a are purged to empty the line of any previous liquid. This is effected by opening one of the valves in selector valve 478 and flowing wash fluid through supply line 480 and through bleed lines 482. Opening valve 487 allows a vacuum force to be transmitted through line 490a through line 488 providing suction which in conjunction with fluid pressure is used to purge the distribution manifold through bleed lines 482. Once wash fluid supply line 480 and distribution manifold are purged, valve 487 is closed and the wash tank is raised and filled. The fill level of wash tank 440 is controlled by the selected wash fluid fill time and wash fluid pressure. Overflow port 486 acts as a safety drain to drain off fluid overfill. If the fluid level within wash tank 440 is too high, liquid will flow from wash tank 440 into overflow port 486 and into line 486a. When valve 487 is open, the suction force from line 490a and 488 will draw overflow liquid from overflow port 486 into waste bottle 490. Restriction flow valve 441 limits liquid fluid flow through lines 482.

FIG. 8F shows the top perspective of wash fluid tank 440. An input line introduces a wash solution into wash fluid distribution manifold 480a. This manifold supplies wash fluid ports 481 that fill tank 440. The spacing of wash fluid ports 481 aids in uniform filling across the width of tank 440. The fill time and fluid pressure regulate the amount of fluid filling tank 440. If excess fluid enters tank 440 it will drain from overflow port 486.

To empty the tank, the tank is lowered by the pneumatics as described, and drain 484 is opened. The shape of tank 440 directs fluid to drain 484 when the end of tank 440 containing drain 484 is lowered. This configuration is designed for efficient filling, emptying and purging of tank 440 and associated fill lines.

Again with reference to FIG. 8E, once a wash cycle has been completed, any liquid remaining within wash manifold interior 425 may be eliminated by opening valve 491 while suction is applied through the manifold. Opening valve 491 causes a pulse of air to be drawn in through vent 493. The air is introduced into wash manifold interior 425 through purge lines 423a and is removed by suction lines 424a. If the manifold is in contact with capillaries, the relatively narrow bores of the capillaries in the capillary cassette provide a limited capacity for drawing air through the wash manifold. By opening valve 491, a much greater amount of air may be drawn through the manifold through purge lines 423a which have a much greater capacity for drawing air. This will result in a sudden rush of air drawn through the manifold. This acts to clear the wash manifold of any liquid remaining within the wash manifold interior 425. Preferably manifold interior 425 is purged before and after raising the wash manifold.

With reference to FIG. 8B, the wash station 410 is shown in side view. The capillary cassette platform 414 is mounted on support legs 445. The reservoir section, shown in internal cross section has at a back lower end of the reservoir, drain outlet 484. Upwardly positioned from the drain outlet at the back wall of the tank is overflow outlet 486. Disposed at the front of the reservoir is reservoir bleed outlet 446. Each outlet is associated with a respective tube and valve, as described in conjunction with FIG. 8E. Each tube carries liquid flowing from an associated outlet when the associated valve is opened and vacuum source applied.

Capillary cassette platform 414 is held in a fixed position by support legs 445. Extending downward from the front of capillary cassette platform 414 is hinge 418 with pivot 432. Attached to a lower end of hinge 418 is wash tank stage 416.

Extending from below wash tank stage 416 is leg 419 that is attached at a lower end by pivot 443 to pneumatic cylinder 429. At the back end of the stationary capillary cassette platform 414, the wash manifold is attached at pivot 420. When pneumatic cylinder 429 is extended from the lower end, wash tank stage 416 will be lowered in an arc away from stationary capillary platform. This occurs when no pressure is applied to 429 and gravity causes the wash tank stage to pivot down. When pneumatic cylinder 429 is extended from the upper end by applied pressure, wash manifold 412 will be raised in an arc away from capillary cassette platform 414.

Disposed above capillary cassette platform 414 is wash manifold 412. The wash manifold has a purge passageway 423 disposed at a front end and a suction passageway 424 disposed toward the back end. The respective lines carrying air to the manifold or removing gas or liquids from the manifold are described in conjunction with FIG. 8E.

With reference to FIG. 8C, pneumatic cylinder 429 is shown fully extended from a lower connection pivot 443 on leg 419, through hole 333 in capillary cassette platform 414, to an upper connection at pivot 428 on wash manifold 412. The extended height of the wash manifold is limited by plate 430 that is secured to the top of manifold 412. Plate 430 abuts pin 422 on capillary cassette platform 414 when the wash manifold is raised to a selected level and prevents the wash manifold 412 from being raised beyond this level. When suction is applied to wash manifold interior 425 by applying suction through suction passageway 424, fluid is drawn through capillaries 12 from tank 440.

The front end of capillary cassette platform 414 is joined at pivot 432 to hinge 418 and wash tank stage 416 and the back end of capillary cassette platform 414 is joined at pivot 420 to wash manifold 412. Extending through capillary cassette platform 414 is cutout 434. The dimensions of cutout 434 are such that capillary cassette 15, when placed on capillary cassette platform 414 has associated capillary tube segments 12 extending through capillary cassette platform 414 while the four edges of capillary cassette substrate 10 are retained on the capillary cassette platform 414 on the edge of cutout 434. Alignment pins may be added to capillary cassette platform 414 to properly position the capillary cassette.

To effect the cassette wash sequence, an electronic controller implements a sequence of steps. The electronic controller instructs associated controlled devices of the wash station to carry out a programmed wash sequence. The programmed sequence begins with the capillary cassette being placed on the capillary cassette stage by the robotic transfer device. The wash manifold lowers onto the capillary cassette such that the shorter end of capillary tube segments extend into the wash manifold and the opposite end of the capillary tube segments are within the wash liquid in the wash tank once filled. The substrate provides a partial seal between the wash manifold and cassette such that when suction is applied to the capillary tube segments by the wash manifold, fluid will be drawn up into the wash manifold through the capillary tube segments. The wash solution supply line is purged with the first selected solution to clear the previous solution from the line. As noted in relation to FIG. 8E, the purge solution is removed through distribution manifold to drain 484 and bleed lines 482 to wash waste line 488 and 490a then into waste bottle 490. The wash tank 440 is then raised and filled with the selected wash solution.

A vacuum is applied to the wash manifold causing the solution in the wash tank to be drawn up through all of the capillary tube segments in the capillary cassette. After the programmed wash duration, the wash tank is drained and lowered. The vacuum force is continued through the wash manifold, drawing air through the capillary tube segments. Once the capillary tube segments are dried, the vacuum line of the wash manifold is turned off. The wash solution supply line is purged with the next wash solution and the steps of raising and filling the wash tank, drawing the wash solution through the capillary tube segments and emptying the wash tank are repeated for each selected solution. The specified sequence may repeat these steps for any number of wash solutions. After the final wash has been completed and the tank emptied, air is drawn through the capillaries by applying a vacuum to the wash manifold, drying the capillary tube segments. Periodically the purge valve 491 is opened and air is drawn through vent 493 into purge lines 423a into purge inlets 423. This draws a blast of air through wash manifold interior 425 and clears the wash manifold interior of any remaining liquid, ensuring that any remaining liquid within the wash manifold will not wick back into the capillaries. The manifold vacuum is then shut off and the manifold is raised, removing the manifold from the capillary cassette. The manifold vacuum is again applied and the purge valve 491 is opened and air is drawn through vent 493 into purge line 423a into purge inlet 423. This ensures that any remaining liquid is removed from the wash manifold interior. The vacuum is then shut off. The washed and dried capillary cassette may then be moved by the transfer robot to a capillary cassette hotel or other location.

System Integration

The components of the system could be integrated in a combined system that allows several elements of the complete system of FIG. 1 to operate at the same time. For example, electronic control device 123 may be used to send instructions to the components of the integrated system. The electronic control device may be a computer that sends electronic signals to various system components to effect a programmed set of instructions. Elements of the system could operate simultaneously, increasing system efficiency. For example, automated robot 102 could retrieve a capillary cassette from cassette hotel 106, place the capillary cassette in a sample plate at stage a. An amount of sample from the plate is drawn into the capillary tubes by capillary action. The capillary cassette could then be moved and placed on top of a microtiter plate such that the short ends of the capillary tube segments are in the wells of the microtiter plate. The robot 102 could then transfer the combined microtiter plate/capillary cassette to dispense location 122 for dispensing. The movement of the robot 102, transfer head 104 and dispensing device located at location 122 are controlled by electronic control device 123.

At the same time that a reaction mixture is being assembled, the electronic control device could also be sending electronic signals to thermocycler 116. The vent door, heating element, and thermocouple of thermocycler 116 could be linked to electronic control device 123, allowing electronic control device 123 to effect a selected temperature cycling procedure by regulating the temperature at which air is cycling within the thermal cycler. This precise monitoring allows the temperature cycling procedure to be effected in a minimum amount of time. Once the thermal cycling procedure is complete, the electronic control device 123 could electronically instruct the thermal cycler to shut off the thermocycler fan and heating element and open the lid pneumatically to allow a capillary cassette to be removed from the interior of the thermal cycler.

While automated robot 102 is moving capillary cassettes to assemble a reaction mixture and the thermocycler is operating, the cassette washer 118 could also be cleaning a capillary cassette. Again the electronic control device 123 could instruct the cassette washer 118 to perform a wash sequence in which a capillary cassette is cleaned with a selected sequence of wash liquids and air-dried.

Electronic control device 123 enables each element of the system to be used with maximum efficiency. A single set of instructions to electronic control device 123 could allow assembly of the reaction mixture, thermal cycling of the reaction mixture to effect the desired reaction, dispensing of the completed reaction mixture onto an analytical substrate, movement of the analytical substrate to a stage for processing by an analytical instrument, and cleaning of used capillary cassettes.

E. Reaction Preparation Examples

The following examples illustrate the use of the combined reaction preparation systems. The examples are representative of the many different types of reactions that could be effected with the disclosed device or system and are described by 1) dye-primer DNA sequencing, 2) dye-terminator DNA sequencing, 3) PCR amplification, 4) PCR amplification, enzymatic purification, and DNA sequencing, and 5) a general enzymatic reaction.

Example 1: Dye-primer DNA sequencing Analyzed by CAE.

Dye-primer sequencing reactions were performed within a capillary cassette comprised of 96 uncoated 2.8 cm long, 150 µm I.D., 360 µm O.D. fused-silica capillaries. Dye-primer sequencing reactions were performed by amplifying template DNA with emission-specific primers corresponding to ddT, ddA, ddC, and ddG terminated reactions. The amplification of template was performed as single reactions in each capillary and pooled into a common well for post-reaction processing and analysis.

The color-specific primers were based on the M13-40 FWD primer (5'-FAM-GTTTTCCCAGT*CACGACG-3'), with 5-carboxyfluorescein (FAM) as the donor dye, and a termination-specific fluor attached to the indicated thymine (T*) as the acceptor dye. The thymine was labeled with FAM for ddc-terminated reactions (C-FAM), 6-carboxyrhodamine for ddA reactions (A-REG), N,N,N',N'-tetramethyl-5-carboxyrhodamine for ddG reactions (G-TMR), and 5-carboxy-X-rhodamine for ddT reactions (T-ROX). A master mix for 100 dye-primer sequencing reactions was prepared by combining 65 µL reaction buffer (220 mM Tris-HCl, pH 9.5, 33.2 mM $MgCl_2$), 100 µL dye-primer solution (either 1 µM T-ROX, 1 µM G-TMR, 0.5 µM A-REG, or 0.5 µM C-FAM), 100 µL of the corresponding deoxy- and dideoxynucleotide mix (0.94 mM DATP, dCTP, dTTP, 7-deaza-dGTP, with 3.1 µM dideoxynucleotide), 10 µL of enzyme (32 units/µL ThermoSequenase), and 225 µL filtered deionized water. This solution was aliquoted into a 96-well reagent plate prior to mixing with template DNA. The general mixing scheme required the use of two capillary cassettes and a 384-well "mix plate". The first capillary cassette (transfer cassette) was dipped in a solution of template DNA (20 ng/µL M13mpl8), and then inverted onto the top of a 384-well "mix plate" with the short ends of the capillaries. inserted into the wells. The inverted transfer cassette and mix plate were placed inside a benchtop centrifuge. A balance plate was added to balance the rotor and the centrifuge brought to 3,000×g for 5 seconds. The centrifugation uniformly dispensed the contents of the transfer cassette into individual wells of the 384-well plate. After the centrifuge step, the transfer cassette was transferred to the capillary cassette washer 410 for cleaning, and the mix plate was used for a subsequent centrifuge step for reagent addition.

To add reagents, a second capillary cassette, (the reaction cassette), was dipped into the wells containing sequencing reagents (prepared as described in the preceding paragraph) and inverted over the same wells of the same 384-well plate. The reaction cassette and mix plate were placed in the centrifuge, spun at 3,000×g for 5 seconds, and removed from the centrifuge. At this point each well contained 500 nL of template DNA and 500 nL of sequencing reagents to form the final reaction mixture. The second capillary cassette (used to add reagents) was then dipped into the 1 µL mixture contained in the mix plate, filling the capillaries of the reaction cassette with 500 nL.

The capillary cassette was inserted into the internal chamber of an air-based thermal cycler, as described herein in FIG. 7A–C, where the ends of the capillary segments are sealed by depressing the ends of the capillaries against deformable membranes 264a and 264b. After 30 cycles of 95° C. for 2 seconds, 55° C. for 2 seconds, and 72° C. for 60 seconds, the thermal cycler was opened, removing the ends of the capillaries from contact with the deformable membranes. The capillary cassette was removed and placed on top of a 96-well "pooling plate" with the short ends of the capillaries inserted into the wells. The capillary cassette and mix plate were placed into a centrifuge, with a balance plate. The reaction products were dispensed by centrifugal force (~2500×g) into a microtiter plate containing 40 µL of 80% isopropyl alcohol. After an initial reaction, the capillaries were washed as described herein. After the four dye-primer reactions had been performed in four individual capillary cassettes and the four sets products pooled into the wells of the 96 well pooling microtiter plate, the samples were subsequently centrifuged at 3000×g for 30 minutes. The alcohol was decanted by a gentle inverted spin, and the samples were resuspended in 5 µL of ddH20 for electrokinetic injection and analysis by MegaBACE capillary array electrophoresis.

Analysis of the DNA sequencing fragments was performed with MegaBACE, a 96-capillary array electrophoresis instrument (Molecular Dynamics, Sunnyvale, Calif.) using scanning confocal laser-induced fluorescence detection. Separations were performed in 62 cm long, 75 µm I.D., 200 µm O.D. fused-silica capillaries with a working separation distance of 40 cm. Electroosmotic flow was reduced by Grignard coupling of a vinyl group to the capillary surface and acrylamide polymerization. The capillaries were filled with a fresh solution of 3% linear polyacrylamide (LPA)(MegaBACE Long Read Matrix, Amersham Life Sciences, Piscataway, N.J.) which was pumped through the capillaries under high-pressure from the anode chamber to individual wells of a 96-well buffer plate contained in the cathode chamber. Each well was filled with 100 µL of Tris-TAPS running buffer (30 mM Tris, 100 mM TAPS, 1 mM EDTA, pH 8.0). The matrix was equilibrated for 20 minutes followed by pre-electrophoresis for 5 minutes at 180 V/cm. Prior to sample injection, the cathode capillary ends and electrodes were rinsed with double distilled water ($ddH_2O$) to remove residual LPA prior to sample injection.

DNA sequencing samples were electrokinetically injected at constant voltage from a 96-well microtiter plate according to the specified conditions; one preferred injection condition for 500 nL samples is 40 seconds of injection at an applied voltage of 2 kV. After injection, the capillary ends were rinsed with water, the buffer plate was placed in the cathode chamber, and the electrophoresis run was commenced. Separations were typically for 120 minutes at 8 kV. Computer controlled automation of the instrument and data collection was performed using LabBench software (Molecular Dynamics, Sunnyvale, Calif.). Specific injection and run conditions were tailored to the reaction mixture to be analyzed.

The reproducibility of the described method for submicroliter dye-primer cycle sequencing is shown in FIG. 9. This histogram shows the percent of samples in different readlength bins and shows that the method is highly reproducible. Over 80 percent of the sequenced DNA inserts had readlengths over 600 bases. Overall, this plate of 96 samples yielded 55,000 high quality "Phred 20" bases, with an average readlength of 605 bases.

Example 2: Dye-primer DNA Sequencing Analyzed by a CAE Microchip.

In another analysis example, dye-primer reactions performed in the same capillary cassette were analyzed by direct injection into a 16 channel microfabricated "chip-based" analyzer described in detail in S. Liu, H. Ren, Q. Gao, D. J. Roach, R. T. Loder Jr., T. M. Armstrong, Q. Mao, I. Blaga, D. L. Barker, and S. B. Jovanovich, Proc. Natl. Acad. Sci. USA, 5-00. The 16-channel chip is formed by bonding two glass wafers, the top wafer has 50 um deep by 100 um wide channels etched into it by standard microfabrication methods. The pattern etched has a combination of two 8-channel groups, each with a common anode reservoir. Sixteen cathode reservoirs were evenly spaced at 4.5-mm intervals in a line, as were sixteen sample and sixteen waste reservoirs. The reservoirs were formed by the drilled access holes through the top etched wafer. Sixteen 250-$\mu$m long twin-T injectors were formed by the offset of channels from the sample and waste reservoirs joining the main separation channel. The distance between adjacent channels (center-to-center) was 600 $\mu$m in the detection region. The two alignment holes were used to align the chip to the detector. In this example, a dye-primer reaction terminated by ddT was performed as described and dispensed into the sample wells of a microchip containing 1.5 $\mu$L of ddH$_2$0. Sample injection was performed by applying voltages of 50 and 10 volts respectively to the waste and cathode reservoirs, typically for 60 s, while the sample and anode reservoirs were grounded. Separations were carried out immediately after sample injection by applying 2,000 volts to the anode reservoir, 140 volts to sample and waste reservoirs, while grounding the cathode reservoir. The corresponding separation field strength was ca. 227 V/cm. The laser-induced fluorescence was collected, digitized, and processed into the electropherogram shown in FIG. 10. The electropherogram demonstrates microchip analysis of the reactions performed in the described capillary cassette system.

Example 3: Dye-terminator Cycle Sequencing with Alcohol Precipitation Purification.

Dye-terminator cycle sequencing was demonstrated using the capillary cassette system and alcohol precipitation for cleanup prior to capillary array electrophoresis. In this example, the sequencing reaction mix was prepared by mixing 400 $\mu$L of sequencing reagents (Dyenamic ET terminator kit, Amersham Pharmacia Biotech, Part 81600) with 100 $\mu$L of 5 pmol/$\mu$L of M13-28 FWD primer (5'-TGT AAA ACG ACG GCC AGT-3'). The reaction mix was distributed in 5 $\mu$L aliquots to a 96-well "reagent" plate. Mixing of template DNA and sequencing reagents was performed in the same series of steps described in Example 1, using a transfer cassette was used to transfer 500 nL of DNA samples and a reaction cassette to transfer 500 nL of sequencing reagents from the reagent plate to the wells of the mix plate. This same reaction cassette was then filled by capillary action with the template/reagent mixture.

The capillary cassette was transferred to the air-based thermal cycler where the capillaries were sealed between the deformable membranes within the thermal cycler. Thermal cycling was achieved with 30 cycles of 95° C. for 2 seconds, 55° C. for 2 seconds, and 60° C. for 60 seconds. After the thermal cycling, the cassette was removed from the cycling chamber and the contents of the capillaries dispensed by centrifugal force (3000×g) into a 96-well plate containing 40 $\mu$L of 80% ethanol. The samples were centrifuged at 3000×g for 30 minutes. The alcohol was decanted by a gentle inverted spin, and the samples were resuspended in 5 $\mu$L of ddH20 for electrokinetic injection and analysis by MegaBACE capillary array electrophoresis. The cleanup of dye-terminator reactions by alcohol precipitation, the reproducibility of the technique, and the application to "real-world" templates is represented as a histogram of percent success versus readlength in FIG. 11. FIG. 11 demonstrates excellent readlengths and success rates with M13 subclone inserts prepared from a subclone library of a mouse bacterial artificial chromosome.

Example 4. Dye-terminator Cycle Sequencing with Size-exclusion Purification.

In another example, dye-terminator reactions were performed in 500 nL capillaries as described in Example 3, and the reaction products dispensed into 15 $\mu$L of ddH20 by centrifugal force. The 15 $\mu$L samples were transferred to a filter plate containing 45 $\mu$L of hydrated Sephadex G-50. The samples were centrifuged through the Sephadex matrix at 910×g for 5 minutes and the eluent collected in a clean 96-well injection plate. The samples were electrokinetically injected without further dehydration or processing into MegaBACE. For 16 samples, an average readlength of 650 bases was obtained demonstrating the compatibility of sub-microliter dye-terminator sequencing with size-exclusion purification.

Example 5. PCR Amplification of Plasmid Insert DNA

The present technology uses the disclosed system for the PCR amplification of insert DNA (e.g. subclone inserts from a DNA library). The PCR reaction mixture was prepared by mixing 5 $\mu$L of 10 $\mu$M of M13-40 FWD primer (5' GTT TTC CCA GTC ACG AC 3') and 5 $\mu$L of 10 $\mu$M M13-40 REV primer (5' GGA TAA CAA TTT CAC ACA GG 3') with 25 $\mu$L of 10×GeneAmp buffer, 15 $\mu$L of 25 mM MgCl$_2$, 5 $\mu$L of AmpliTaq Gold, 2.5 $\mu$L of 1 mg/mL bovine serum albumin (BSA), and 67.5 $\mu$L of ddH$_2$0. This mix was aliquoted in equal volumes to sixteen 0.20 mL tubes.

The reaction was initiated by mixing template DNA with the PCR cocktail using the two-capillary cassette and mix-plate method described. The transfer cassette was dipped into the glycerol stock solutions of a subclone library and dispensed by centrifugal force into the wells of a 384-well plate. A second "reaction" cassette was used to transfer 500 nL of PCR cocktail to the same wells by centrifugal force. The capillaries of the reaction cassette were subsequently dipped into the combined mixture of template DNA and PCR reagents, filling the capillaries by capillary action. Amplification was effected by placing the capillaries into the cycling chamber and thermally cycling with an activation step of 95° C. for 12 minutes followed by 30 cycles of 64° C. for 4.5 minutes and 95° C. for 5 seconds.

The PCR products were analyzed by agarose gel electrophoresis and compared with the same subclones amplified by full volume (25 $\mu$L) reactions performed in 0.20 mL tubes. Nanoscale capillary cassette samples were dispensed into 4.5 $\mu$L of ddH$_2$0 by centrifugal force. Equivalent volume aliquots of full volume reactions were transferred manually using a low volume pipettor. To each 5 $\mu$L sample, 1 µL of 6×loading dye was added and the sample quantitatively transferred to the wells of an agarose gel. Agarose gel electrophoresis was performed using a 0.7% agarose gel with 1×Tris-acetate-EDTA buffer, pH 8.0. Samples were separated for 40 minutes at 15 V/cm, stained with Sybr Green II (Molecular Probes, Eugene, Oreg.), and imaged using a two-dimensional fluorescence scanner (FluorImager, Molecular Dynamics, Sunnyvale, Calif.). The scanned gel image is shown in FIGS. 12A and 12B. It can be seen that samples prepared at full volume (FIG. 12A) and 500 nL volume (FIG. 12B) have the same molecular weight distribution. This example demonstrates nanoscale sample preparation can be used for PCR reactions and that the products can be analyzed by traditional macro-scale analysis methods such as agarose gel electrophoresis.

Example 6. PCR Amplification and Cycle-sequencing.

A preferred mode of preparing cycle sequencing samples using the present invention is to prepare nanoscale PCR samples in the capillary cassette and related instrumentation, perform macroscale ExoI/SAP reactions, and then perform the cycle sequencing in the capillary cassette and related instrumentation. Nanoscale PCR template preparation for DNA sequencing was demonstrated by performing PCR amplification from glycerol stock subclones. Glycerol stock subclones were PCR amplified in the capillary cassette and related hardware as described in Example 5. After PCR amplification, the contents of the capillaries were dispensed by centrifugation into the wells of a 96-well plate containing 4.5 µL of 7.5 mU of shrimp alkaline phosphatase (SAP) and 37.5 mU of exonuclease I (ExoI). The PCR products and ExoI/SAP solution were allowed to incubate at 37° C. for 5 minutes to digest the unincorporated primers and to dephosphorylate the unincorporated nucleotides. After an initial incubation, the enzymes were deactivated by heating the solution to 72° C. for 15 minutes.

The ExoI/SAP treated PCR products were aliquoted to a fresh 384-well mix plate with a transfer capillary cassette and centrifugal dispensing. An equal aliquot of dye-terminator sequencing reagents were added to the 500 nL of purified PCR products using another capillary cassette, the reaction cassette, and centrifugal dispensing. The capillaries of the reaction cassette were then filled by dipping the capillary cassette into the 1 µL reaction mixture. The template was amplified according to Example 3, dispensed into 40 µL of 80% ethanol and purified as described. Analysis of the sequencing reactions was performed by MegaBACE using electrokinetic injection. Portions of six basecalled sequencing electropherograms from subclone templates prepared by nanoscale PCR amplification from glycerol stock solutions and by nanoscale cycle sequencing are shown in FIG. 13. By performing PCR in a capillary cassette and subsequently transferring the reaction mixture to a microplate, the present system allows a simplified transition from nanoscale (less than 1 µL volumes) to greater than nanoscale reaction volumes. The present system also allows a simplified transition from macroscale (more than 1 µL volumes) to nanoscale reaction volumes, as shown by utilizing the Exo I/SAP reactions for cycle sequencing in the capillary cassette.

Example 7. Isothermal Enzyme Assay Performed in Sub-microliter Capillary Cassette.

The use of the described system for performing general enzyme reactions was demonstrated with a fluorogenic enzymatic assay of β-galactosidase hydrolysis of resorufin-β-D-β-galactosidase to the fluorophore resorufin. The β-galactosidase catalyzed hydrolysis of resorufin-β-D-galactosidase (RBG) was performed within the capillaries of a 96-capillary cassette and in control full volume reactions in which β-Gal hydrolyzes RBG.

A stock solution of 350 µM RBG was prepared in 5 mL of buffer (100 mM Tris-HCL, 20 mM KCl, and 2 mM $MgCl_2$) to 5 mg of RBG, vortexing vigorously, and filtering the solution through a 0.40 micron filter and then adding an equal volume of buffer. A dilution curve of RBG was then prepared from the stock solution. To each 10 µL of RBG solution prepared in 0.20 mL tubes, 200 ug of β-galactosidase was added and after briefly mixing, filled into a capillary cassette by capillary action. The cassette was placed in an air cycler and after 2 minutes at 37° C., the capillary cassette was removed and the contents centrifuged out of the capillaries into a 384-well scan plate containing 5 uL of 1 M sodium carbonate. The wells of the scan plate were subsequently filled with 50 µL of ddH20. In parallel, the 0.2 mL tubes were incubated at 37° C. for 2 minutes and the full volume reactions stopped by adding 1 M sodium carbonate. A control aliquot from the enzyme reactions performed in the 0.20 mL tubes was added to the scan plate.

Solid-phase capture of the β-galactosidase was also demonstrated with this system by simply filling the cassette with a 20 ug/mL solution of β-galactosidase, allowing the β-galactosidase to bind to the capillary surface followed by removing the excess liquid and drying the cassette using the described cassette wash-manifold. After β-galactosidase binding the capillaries were filled with RBG solution by capillary action. The reaction was performed for 2 minutes at 37° C. and analyzed by dispensing into 1 M sodium carbonate, and diluting with water in the scan plate.

Once all three sets of reactions (full volume, capillary cassette, and capillary cassette with solid phase capture) had been added to the scan plate, the plate was read by a fluorescent plate reader (Typhoon, Molecular Dynamics, Sunnyvale, Calif.).The results of the standard curve performed in 0.2 mL tubes (tube rxn), a reaction performed in the capillary cassette without solid phase capture (capillary reaction), and in the capillary cassette with solid phase capture (capillary with binding reaction) are summarized in FIG. 14. FIG. 14 shows the expected signal versus substrate concentration for the tube reactions, and data points of signal for the pre-mixed enzyme reaction performed in the capillary cassette, and for the capillary-binding β-galactosidase assay.

This example serves to illustrate the compatibility of the described system for performing a range of general enzyme activity and inhibition assays. In addition, it demonstrates that solid phase capture can be applied to proteins and enzymes as well as DNA. Finally, it shows the described system can be applied to isothermal reactions.

What is claimed is:

1. A system for performing small scale reactions, the system comprising:
a capillary cassette having a substrate and a plurality of capillaries extending through said substrate, wherein each of said capillaries has first and second open ends on opposing sides of said substrate;
a pair of membranes orientated and spaced such that they may temporarily seal the opposed ends of said capillaries;
a thermal cycler having an internal chamber of sufficient capacity to hold said capillary cassette and said membranes; and
an automated transfer device positioned to contact and move the capillary cassette to a location where the ends of the capillary may be sealed by the pair of membranes and the capillary cassette with ends sealed by said membranes may be located within the internal chamber of the thermal cycler.

2. The system of claim 1, further comprising a dispenser that dispenses a fluid from capillaries of the capillary cassette onto a location on a receiving substrate, wherein the automated transfer device may move the capillary cassette in relation to said dispenser and receiving substrate such that the fluid contained within the capillaries of the capillary cassette are dispensed onto the substrate.

3. The system of claim 2, wherein the dispenser is a centrifuge.

4. The system of claim 2, wherein the dispenser is an air displacement dispenser.

5. The system of claim 2, further comprising an analytical stage positioned such that the automated transfer device may transfer said capillary cassette in relation to said dispenser such that contents within said capillary cassette may be dispensed onto a substrate located upon said stage.

6. The system of claim 5, wherein said substrate is a sample preparation microchip and the automated transfer device is disposed to dispense the capillary cassette directly into a plurality of sample preparation microchip sample receiving wells.

7. The system of claim 5, wherein said substrate is an array of capillaries and the automated transfer device is dispersed to disperse the capillary cassette directly into the capillaries.

8. The system of claim 2, wherein said substrate is a multiwell plate.

9. The system of claim 1 wherein the capillaries have an interior volume of 10–1000 nL.

10. The system of claim 1, further including a capillary cassette wash station, wherein said automated transfer device may transfer a capillary cassette into contact with said wash station, said wash station directing a wash solution through the capillaries of the capillary cassette when said capillary cassette is placed within said wash station.

11. The system of claim 10, wherein said wash station has a wash solution tank and an upper wash manifold that may be moved to a position above said wash solution tank, wherein a wash fluid may be introduced into said wash solution tank and drawn by suction into the wash manifold when the capillary cassette is inserted into said wash station.

12. The system of claim 11, wherein said wash station further includes a plurality of wash fluid bottles each containing a wash fluid and a selector valve allowing selection of a wash fluid from one of said bottles to fill said wash solution tank.

13. The system of claim 1, further comprising an electronic control which may be programmed to send electronic instructions to components of the system.

14. The system of claim 1 wherein said pair of membranes are affixed to opposing sides of the internal chamber of the thermal cycling device.

15. The system of claim 1 further comprising a plurality of microplate holder magazines which dispense microplates to a location where said automated transfer device may contact and move the microplates.

16. The system of claim 1 wherein said membranes are deformable membranes held with a spring bias to temporarily seal the ends of the capillaries.

17. A system for nanoscale reaction preparation, the system comprising:

a capillary cassette including a substrate and a plurality of capillaries extending through said substrate, each capillary having an internal volume of between 10 nl and about 1 uL, wherein each of said capillaries has a first and a second open end on opposing sides of said substrate, wherein the length of the capillary extending through substrate on one side of the substrate is matched to be shorter than the depth of a microplate well;

a multiwell plate having a plurality of wells into which the capillaries of the capillary cassette may be inserted;

a dispenser that dispenses fluid contained within the capillaries of the capillary cassette into wells of said multiwell plate when said capillary is transported to the dispenser;

an automated transfer robot having a transfer head to carry articles selected from the group comprising capillary cassettes, multiwell plates, and multiwell plates with capillaries of a capillary cassette inserted into the wells of the multiwell plates;

a pair of opposing membrane surfaces, wherein the ends of the capillaries may be temporarily sealed by pressing the membranes against said ends; and a thermal cycler having an internal chamber of sufficient capacity to hold said capillary cassette and said membranes when said membranes are sealing the ends of the capillaries of the capillary cassette, wherein the thermal cycler is disposed such that the automated transfer robot may place a capillary cassette into an internal chamber within said thermal cycler wherein said membranes may seal the end of the capillaries of said capillary cassette within said internal chamber.

18. The system of claim 17 wherein said dispenser is an electrokinetic injector.

19. The system of claim 17 wherein said dispenser is a centrifuge.

20. The system of claim 17 wherein said dispenser is an air displacement head.

21. The system of claim 17 wherein said dispenser is disposed to dispense liquid from the capillaries onto an analytical substrate located on an analytical stage.

22. The system of claim 17, further comprising a capillary cassette wash station, wherein said automated transfer device may transfer a capillary cassette into contact with said wash station, said wash station directing a wash solution through interiors of the capillaries of the capillary cassette when said capillary cassette is placed within said wash station.

23. The system of claim 22, wherein said wash station includes a lower wash solution tank and an upper wash manifold, wherein a wash fluid may be introduced into said wash solution tank and drawn by suction into the wash manifold when the capillary cassette is inserted into said wash station.

24. The system of claim 23, wherein said wash station further includes a plurality of wash fluid bottles and a selector valve in fluid communication with said bottles for selection of a wash fluid to fill said wash solution tank.

25. The system of claim 17, further comprising an electronic control, said control sending electronic instructions to effect programmed operation of said system.

26. A system for preparing nanoscale reactions, the system comprising:

a substrate having integrally associated elongate submicroliter volume reaction containers having two opposing ends;

a reaction mixture contained within said reaction containers;

a pair of membranes disposed to temporarily seal said opposing ends of said reaction containers;

a thermal cycler having an internal chamber of sufficient dimension to receive said substrate with associated elongate reaction chambers sealed by said membranes.

27. The system of claim 26, wherein said substrate has capillaries extending through said substrate, wherein said capillaries act as the reaction chambers.

28. The system of claim 26, wherein said elongate reaction containers pass through the thickness of said substrate.

29. The system of claim 26, wherein said thermal cycler circulates heated air through a continuous circuit, wherein said internal chamber is part of said continuous circuit.

30. The system of claim 29, wherein said continuous circuit may be vented by blocking a section of said internal passageway and venting said heated air thereby allowing rapid temperature adjustment of said heated air.

31. The system of claim 30, wherein said internal chamber contains said membranes mounted on opposing surfaces of said internal chamber.

32. The system of claim 31, wherein at least one of said membranes is mounted within said internal chamber with a spring bias which provides a sealing force of said membranes against said ends of said reaction containers.

33. The system of claim 26, further comprising a means for dispensing said reaction containers.

34. The system of claim 26, further comprising a means for combining reagents to form said reaction mixture and a means for filling said reaction containers with said reaction mixture.

35. The system of claim 26, further comprising a wash station which may hold and wash said reaction containers.

36. A method to prepare nanoscale thermal cycling reaction mixtures, the steps comprising;

combining compounds to form a reaction mixture;

introducing said reaction mixture into a plurality of reaction containers disposed on a substrate, each reaction container having an internal volume less than one microliter and having a first and second open end;

temporarily sealing the ends of reaction containers by pressing a pair of opposing membranes against a first and second set of reaction container ends;

exposing the sealed reaction containers to temperature cycles to effect a reaction in the reaction mixture; and dispensing the reaction containers onto a substrate.

37. The method of claim 36 wherein the steps of combining compounds to form a reaction mixture includes the steps:

metering an amount of a first liquid reaction component by placing one end of a plurality of capillaries of a capillary cassette into contact with the first liquid reaction component wherein the capillaries fill by capillary action;

dispensing the first liquid reaction component onto discrete locations on a substrate;

metering an amount of a second liquid reaction component by placing one end of the capillaries of a capillary cassette into contact with the reaction reagents wherein the capillaries fill by capillary action; and dispensing the second liquid reaction component onto the discrete locations, thereby combining said first and second liquid reaction components to form a reaction mixture.

38. The method of claim 37 wherein the step of introducing said reaction mixture into a plurality of reaction containers is effected by providing a capillary cassette and dipping one open end of capillaries of the capillary cassette into contact with the reaction mixture so that the capillaries fill by capillary action.

39. The method of claim 36 wherein the steps of combining compounds to form a reaction mixture includes the steps:

immobilizing a biomolecule sample on an interior surface of the reaction container;

metering an amount of reaction reagents into the capillaries of the capillary cassette by placing one end of the capillaries of a capillary cassette into contact with the reaction reagents wherein the capillaries fill by capillary action, whereby the reaction reagents and the immobilized biomolecule combine to form the reaction mixture.

40. The method of claim 39, wherein the biomolecule is a nucleic acid.

41. The method of claim 36 wherein the steps of combining compounds to form a reaction mixture include the steps:

coating a plurality of surface locations with a layer of desiccated reaction reagents; and adding to each surface location a nucleic acid sample in solution of sufficient volume to dissolve the solid layer of reaction reagents, thereby forming a reaction mixture.

42. The method of claim 36 wherein the steps of combining compounds to form a reaction mixture include the steps:

coating an interior surface of each capillary in a capillary cassette with a layer of desiccated reaction reagents; and metering an amount of nucleic acid sample in solution into the capillaries of the capillary cassette by placing one end of the capillaries of a capillary cassette into contact with the nucleic acid sample in solution, whereby the capillaries fill by capillary action, whereby the solution allows the layer of reaction reagents to dissolve, forming the reaction mixture.

43. The method of claim 36, wherein the step of dispensing the reaction containers onto a substrate is effected by:

placing the substrate with associated reaction containers in a centrifuge;

positioning a substrate at a radially distal end of one open end of said reaction containers; and applying centrifugal force such that liquid reaction mixtures contained within said reaction containers are dispensed onto said substrate.

44. The method of claim 36, wherein the step of dispensing the reaction containers onto a substrate is effected by:

displacing the contents of the reaction containers onto a substrate using air displacement.

45. The method of claim 36 wherein the step of temporarily sealing the ends of the reaction containers by pressing a pair of opposing membranes against a first and second set of reaction container ends is effected by:

placing the reaction containers within an interior chamber of a thermal cycler, wherein when the reaction containers are enclosed within said thermal cycler, deformable membranes on opposing interior surfaces of said interior chamber temporarily seal the reaction containers' ends on each end of the reaction containers.

46. The method of claim 36 wherein the step of exposing the sealed reaction to temperature cycles to effect a reaction is effected circulating heated air past the reaction containers through a conduit which allows rapid venting of air to the exterior of said conduit to effect rapid temperature changes during the temperature cycles.

47. A thermal cycling device for exposing reaction mixtures to temperature cycles, the device comprising:
a housing enclosing a continuous interior circuit passageway, said housing having a section that may be temporarily opened to allow access to the interior of the housing;
a blower disposed within said circuit passageway to direct air flow in one direction in the internal circuit passageway;
a heating element disposed in said internal circuit passageway such that air circulating within said passageway passes through said heating element;
a sample holding compartment having two membranes positioned in opposing orientation within said sample holding compartment, wherein said membranes may be biased against opposing ends of containers inserted into the sample holding compartment;
housing air vent which may be opened to rapidly exhaust heated circulating air; and
a housing air intake for drawing air into said interior circuit passageway when the vent exhausts heated circulating air.

48. The thermal cycling device of claim 47 further comprising a temperature monitoring device disposed in the internal passageway proximate to a sample holding compartment.

49. The thermal cycling device of claim 47 further comprising at least one air diffuser disposed in the internal passageway between the blower and the sample holding compartment, said diffuser promoting uniform temperature in the air circulating in the internal passageway.

50. The thermal cycling device of claim 47 wherein at least one of the membranes within the sample holding compartment is spring biased.

51. The thermal cycling device of claim 47 further comprising insulation affixed to the surfaces of the interior circuit passageway.

52. The thermal cycling device of claim 47 further comprising an electronic control which sends instruction to components of the thermal cycling device.

53. The thermal cycling device of claim 47 wherein said vent is opened by moving a section of said housing located between said sample holding compartment and said air intake such that the internal passageway is at least partially restricted and an opening to outside said housing is created.

54. The thermal cycling device of claim 47 wherein the housing has a sealable opening to admit access to the sample holding compartment.

55. A method for performing reactions, the method comprising,
a) introducing reaction mixtures into a reaction container set, each container in the set having two opposing ends and an internal volume between 10 to 1000 nl;
b) temporarily sealing the ends of the reaction chambers by pressing a deformable membrane against the opposing ends of said reaction containers;
c) effecting a reaction within said reaction containers;
d) dispensing reaction mixtures onto discrete locations on a substrate; and
e) combining said reaction mixtures with at least 1 $\mu$l of a liquid reagent mixture.

56. The method of claim 55, further comprising the step of:
f) reacting the completed reaction mixture with the liquid reagent mixture.

57. The method of claim 56, further comprising the step of:
g) combining reacted mixtures of step f with a reaction reagent set to form a second reaction mixture set;
h) introducing said second reaction mixture set into a second reaction container set, each reaction container having two opposing ends and an internal between 10 and 1000 nl;
i) temporarily sealing the ends of the set of reaction containers by pressing deformable membranes against the opposing ends of said reaction containers;
j) effecting a reaction within said second reaction container set; and
k) dispensing reacted mixtures from said second reaction container set.

58. The method claim 57, wherein step f occurs under isothermal reaction conditions.

59. The method of claim 57, wherein the reaction mixture of step a is a PCR mixture, the liquid reagent mixture of step e contains exonuclease I and shrimp alkaline phospotase, and the second reaction mixture.

60. The method of claim 57 wherein steps c and j include exposing the reaction container sets to temperature cycles.

61. The method of claim 60 wherein the exposing reaction container sets to temperature cycles is effected by a circulating air thermal cycler.

62. The method of claim 57 wherein the second reaction container set is dispensed onto an analytical substrate.

63. The method of claim 57 wherein the second reaction container set is dispensed into the ends of capillaries in a capillary electrophoresis array.

64. The method of claim 57 wherein the second reaction container set is dispensed into the wells of a microplate.

* * * * *